United States Patent [19]

Summers, Jr. et al.

[11] Patent Number: 4,873,259
[45] Date of Patent: Oct. 10, 1989

[54] INDOLE, BENZOFURAN, BENZOTHIOPHENE CONTAINING LIPOXYGENASE INHIBITING COMPOUNDS

[75] Inventors: James B. Summers, Jr., Libertyville; Bruce P. Gunn, Island Lake; Dee W. Brooks, Libertyville, all of Ill.

[73] Assignee: Abbott Laboratories, Abbott Park, Ill.

[21] Appl. No.: 138,073

[22] Filed: Jan. 11, 1988

Related U.S. Application Data

[63] Continuation-in-part of Ser. No. 60,784, Jun. 10, 1987, abandoned, which is a continuation-in-part of Ser. No. 12,970, Feb. 10, 1987, abandoned.

[51] Int. Cl.$^4$ ............ A61K 31/38; A61K 31/34; C07D 209/04; C07D 333/52
[52] U.S. Cl. .................... 514/443; 514/415; 514/418; 514/419; 514/469; 514/470; 548/469; 548/484; 548/485; 548/486; 548/495; 549/49; 549/51; 549/52; 549/54; 549/55; 549/57; 549/58; 549/462; 549/466; 549/467
[58] Field of Search ............ 514/415, 443, 469, 470, 514/418, 419; 549/51, 55, 57, 58, 466, 467, 49, 52, 54, 462; 548/484, 486, 495, 485, 469

[56] References Cited

U.S. PATENT DOCUMENTS

| | | |
|---|---|---|
| 3,855,242 | 12/1974 | Chapman et al. |
| 3,912,748 | 10/1975 | Evans et al. |
| 3,928,384 | 12/1975 | Descamps et al. |
| 4,594,425 | 6/1986 | Musser et al. |
| 4,604,407 | 8/1986 | Haslanger et al. |
| 4,607,053 | 8/1986 | Karanewsky et al. |
| 4,665,206 | 5/1987 | Redpath et al. |

FOREIGN PATENT DOCUMENTS

| | | |
|---|---|---|
| 0196184 | 10/1986 | European Pat. Off. |
| 2068420 | 8/1971 | France. |
| 48-72162 | 9/1973 | Japan. |
| 1231804 | 5/1971 | United Kingdom. |

*Primary Examiner*—Alan Siegel
*Attorney, Agent, or Firm*—Steven F. Weinstock; Steven R. Crowley; Martin L. Katz

[57] ABSTRACT

Compounds of the formula:

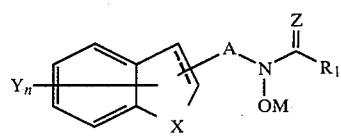

wherein $R_1$ is (1) hydrogen, (2) $C_1$ to $C_4$ alkyl, (3) $C_2$ to $C_4$ alkenyl, or (4) $NR_2R_3$, wherein $R_2$ and $R_3$ are independently selected from (1) hydrogen, (2) $C_1$ to $C_4$ alkyl and (3) hydroxyl, but $R_2$ and $R_3$ are not simultaneously hydroxyl;

wherein X is oxygen, sulfur, $SO_2$, or $NR_4$, wherein $R_4$ is (1) hydrogen, (2) $C_1$ to $C_6$ alkyl, (3) $C_1$ to $C_6$ alkoyl, (4) aroyl, or (5) alkylsulfonyl;

A is selected from $C_1$ to $C_6$ alkylene and $C_2$ to $C_6$ alkenylene;

n is 1–5;

Y is selected independently at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) $C_1$–$C_8$ thioalkyl, (11) aryl, (12) aryloxy, (13) aroyl, (14) $C_1$ to $C_{12}$ arylalkyl, (15) $C_2$ to $C_{12}$ arylalkenyl, (16) $C_1$ to $C_{12}$ arylalkoxy, (17) $C_1$ to $C_{12}$ arylthioalkoxy, and substituted derivatives of (18) aryl, (19) aryloxy, (20) aroyl, (21) $C_1$ to $C_{12}$ arylalkyl, (22) $C_2$ to $C_{12}$ arylalkenyl, (23) $C_1$ to $C_{12}$ arylalkoxy, or (24) $C_1$ to $C_{12}$ arylthioalkoxy, wherein substituents are selected from halo, nitro, cyano, $C_1$ to $C_{12}$ alkyl, alkoxy, and halosubstituted alkyl;

Z is oxygen or sulfur;

and M is hydrogen, a pharmaceutically acceptable cation, aroyl, or $C_1$ to $C_{12}$ alkoyl, are potent inhibitors of 5- and/or 12-lipoxygenase enzymes.

Also disclosed are lipoxygenase inhibiting compositions and a method for inhibiting lipoxygenase activity.

25 Claims, No Drawings

INDOLE, BENZOFURAN, BENZOTHIOPHENE CONTAINING LIPOXYGENASE INHIBITING COMPOUNDS

This application is a continuation-in-part of U.S. application Ser. No. 060,784, file June 10, 1987 now abandoned, which is a continuation-in-part of U.S. application Ser. No. 012,970, filed Feb. 10, 1987 now abandoned.

TECHNICAL FIELD

This invention relates to organic compounds which inhibit lipoxygenase enzymes. It also relates to methods and compositions involving inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs).

Similarly, 12- and 15-lipoxygenase, convert arachidonic acid to 12- and 15-HPETE, respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs $C_4$ and $D_4$ are potent constrictors of human airways in vitro, and aerosol administration of these substances to non-asthmatic volunteers induces broncho-constriction. $LTB_4$ and 5-HETE are potent chemotactic factors for inflammatory cells such as polymorphonuclear leukocytes. They also have been found in the synovial fluid of rheumatoid arthritic patients. Leukotrienes have also been implicated as important mediators in asthma, rheumatoid arthritis, gout, psoriasis, allergic rhinitis, adult respiratory distress syndrome, Crohn's disease, endotoxin shock, inflammatory bowel disease and/or ischemia induced myocardial or brain injury, among others. The biological activity of the LTs has been reviewed by Lewis and Austen (J. Clinical Invest. 73,889, 1984) and by J. Sirois (Adv. Lipid Res. 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes are believed to play an important role in the biosynthesis of mediators of asthma, allergy, arthritis, psoriasis, and inflammation. It is postulated that interrupting the biochemical pathways involved in the various manifestations of these disease states will provide effective systemic and/or symptomatic treatment of these diseases.

DETAILED DESCRIPTION OF THE INVENTION

In accordance with the present invention there are 5- and/or 12-lipoxygenase inhibiting compounds of the formula:

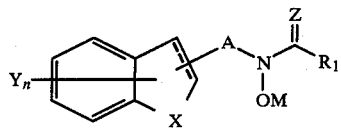

Formula I wherein $R_1$ is (1) hydrogen, (2) $C_1$ to $C_4$ alkyl, (3) $C_2$ to $C_4$ alkenyl, or (4) $NR_2R_3$, wherein $R_2$ and $R_3$ are independently selected from (1) hydrogen, (2) $C_1$ to $C_4$ alkyl and (3) hydroxyl, but $R_2$ and $R_3$ are not simultaneously hydroxyl;

wherein X is oxygen, sulfur, $SO_2$, or $NR_4$, wherein $R_4$ is (1) hydrogen, (2) $C_1$ to $C_6$ alkyl, (3) $C_1$ to $C_6$ alkoyl, (4) aroyl, or (5) alkylsulfonyl;

A is selected from $C_1$ to $C_6$ alkylene and $C_2$ to $C_6$ alkenylene;

n is 1–5;

Y is selected independently at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) $C_1$–$C_8$ thioalkyl, (11) aryl, (12) aryloxy, (13) aroyl, (14) $C_1$ to $C_{12}$ arylalkyl, (15) $C_2$ to $C_{12}$ arylalkenyl, (16) $C_1$ to $C_{12}$ arylalkoxy, (17) $C_1$ to $C_{12}$ arylthioalkoxy, and substituted derivatives of (18) aryl, (19) aryloxy, (20) aroyl, (21) $C_1$ to $C_{12}$ arylalkyl, (22) $C_2$ to $C_{12}$ arylalkenyl, (23) $C_1$ to $C_{12}$ arylalkoxy, or (24) $C_1$ to $C_{12}$ arylthioalkoxy, wherein substituents are selected from halo, nitro, cyano, $C_1$ to $C_{12}$ alkyl, alkoxy, and halosubstituted alkyl;

Z is oxygen or sulfur;

and M is hydrogen, a pharmaceutically acceptable cation, aroyl, or $C_1$ to $C_{12}$ alkoyl.

The dotted line within the five membered ring of formula I signifies that a single or double bond are to be selected from. The substituent(s) Y and the linking group A may be attached at any available position on either ring.

The preferred compounds of the present invention are of formula

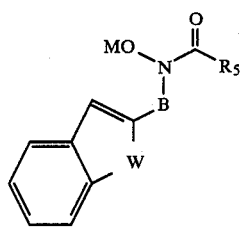

Formula II

In these preferred compounds $R_5$ is $C_1$ or $C_2$ alkyl, or $NR_6R_7$ where $R_6$ and $R_7$ are independently selected from hydrogen and $C_1$ or $C_2$ alkyl; B is $CH_2$ or $CHCH_3$; W is oxygen or sulfur; and M is hydrogen, a pharmaceutically acceptable cation, aroyl, or $C_1$ to $C_{12}$ alkoyl.

Examples of compounds which are within the scope of the present invention include the following:

N-hydroxy-N-(1-benzo[b]thien-2-ylethyl) acetamide

N-hydroxy-N-(1-benzo[b]thien-2-ylethyl) urea

N-hydroxy-N-(1-benzo[b]thien-2-ylethyl) N'-methyl urea

N-hydroxy-N-(1-benzo[b]thien-2-ylethyl) N',N'-dimethyl urea

N-hydroxy-N-benzo[b]thien-2-ylmethyl urea

N-hydroxy-N-benzo[b]thien-2-ylmethyl N'-methyl urea
N-hydroxy-N-benzo[b]thien-2-ylmethyl N',N'-dimethyl urea N-hydroxy-N-(1-benzo[b]thien-3-ylethyl) acetamide
N-hydroxy-N-(1-benzo[b]thien-3-ylethyl) urea
N-hydroxy-N-[1-(3-methylbenzo[b]thien-2-yl)ethyl] urea
N-hydroxy-N-[1-(5-(2,2-dimethylethyl)benzo[b]thien-3-yl)ethyl] urea
N-hydroxy-N-[1-benzo[b]thien-2-ylethyl) acetamide 1,1-dioxide
N-hydroxy-N-(1-benzo[b]thien-2-ylethyl) urea 1,1-dioxide
N-hydroxy-N-(1-benzo[b]fur-2-ylethyl) acetamide
N-hydroxy-N-(1-benzo[b]fur-2-ylethyl) urea
N-hydroxy-N-(1-(1-methylindol-3-yl)ethyl) acetamide
N-hydroxy-N-(1-(1-methylindol-3-yl)ethyl) urea
N-hydroxy-N-(1-(1-methylindol-3-yl)ethyl) N'-methyl urea
N-hydroxy-N-(1-benzo[b]thien-2-yl)ethyl) urea sodium salt
N-hydroxy-N-(1-benzo[b]thien-2-ylethyl) formamide
N-hydroxy-N-(1-benzo[b]thien-2-ylethyl)2-methylpropionamide
N-hydroxy-N-[1-(5-chlorobenzo[b]fur-2-yl)ethyl] urea
N-hydroxy-N-[1-(5-methoxybenzo[b]fur-2-yl)ethyl] urea
N-hydroxy-N-(1-(1-methylindol-2-yl)ethyl) urea
N-hydroxy-N-(1-benzo[b]thien-2-ylethyl) thiourea
N-hydroxy-N-[1-(3-thioethylbenzo[b]thien-2-yl)ethyl] urea
N-hydroxy-N-[1-(5-fluorobenzo[b]thien-2-yl)ethyl] urea
N-hydroxy-N-(2-benzo[b]thien-2-yl-1-methylethyl) urea
N-hydroxy-N-(3-benzo[b]thien-2-ylprop-2-enyl) acetamide
N-hydroxy-N-(3-benzo[b]thien-2-ylprop-2-enyl) urea
N-hydroxy-N-[1-(5-nitrobenzo[b]fur-2-yl)ethyl] urea
N-hydroxy-N-[1-(5,7-dichlorobenzo[b]fur-2-yl)ethyl] urea
N-hydroxy-N-[1-(7-methoxybenzo[b]fur-2-yl)ethyl] urea
N-hydroxy-N-[1-(7-methoxybenzo[b]fur-2-yl)ethyl] N'-methyl urea
N-hydroxy-N-[1-(7-methoxybenzo[b]fur-2-yl)ethyl] urea
N-hydroxy-N-(1-indol-2-ylethyl) N'-methyl urea
N-hydroxy-N-[1-(5-chloroindol-2-yl)ethyl] N'-methyl urea
N-hydroxy-N-[1-(1-acetylindol-2-yl)ethyl] urea
N-hydroxy-N-[1-(1-methanesulfonylindol-2-yl)ethyl] urea
N-hydroxy-N-benzo[b]thien-7-ylmethyl urea
N-hydroxy-N-[1-(2,3-dihydrobenzo[b]fur-yl) ethyl] urea
N,N'-dihydroxy-N-(1-benzo[b]thien-2-ylethyl) urea
N-hydroxy-N-(1-benzo[b]thien-2-ylethyl) N'-ethylurea
N-hydroxy-N-(1-benzo[b]thien-2-ylethyl) N'-methyl thiourea
N-hydroxy-N-benzo[b]thien-2-ylmethyl N'-methyl urea
N-hydroxy-N-benzo[b]thien-2-ylmethyl-N'-ethyl urea
N-hydroxy-N-(1-benzo[b]thien-2-yl)-3-methylpropyl urea
N-hydroxy-N-benzo[b]fur-2-ylmethyl urea
N-hydroxy-N-benzo[b]fur-2-ylmethyl N'-methyl urea
N-hydroxy-N-[1-(6-phenylmethoxybenzo[b]fur-2-yl)ethyl] urea
N-hydroxy-N-[1-(6-phenylmethoxybenzo[b]fur-2-yl)ethyl] N'-methyl urea
N-hydroxy-N-(1-indol-2-yl)ethyl) urea
N-hydroxy-N-[1-(3-hydroxybenzo[b]thien-2-yl)ethyl] urea
N-hydroxy-N-[1-(5-trifluoromethylbenzo[b]thien-2-yl)ethyl] urea
N-hydroxy-N-[1-(7-methoxybenzo[b]thien-2-yl)ethyl] urea
N-hydroxy-N-[1-(5-phenylbenzo[b]thien-2-yl)ethyl] urea
N-hydroxy-N-[1-(5-phenylmethoxy-benzo[b]thien-2-yl)ethyl] urea
N-hydroxy-N-[1-(2-benzo[b]thien-2-yl)propyl] urea
N-hydroxy-N-(1-benzo[b]thien-2-ylethyl) propionamide
N-hydroxy-N-(1-benzo[b]thien-2-ylethyl) propenamide
N-hydroxy-N-indol-2-ylmethyl acetamide
N-hydroxy-N-(1-benzo[b]thien-3-ylethyl) acetamide
N-hydroxy-N-[1-(5-fluorobenzo[b]fur-2-yl)ethyl] acetamide
N-hydroxy-N-(1-(5-phenoxybenzo[b]fur-2-yl)ethyl) acetamide
N-hydroxy-N-[1-(5-(4-fluorophenyl)methyl)benzo[b]thien-2-yl)ethyl] acetamide
N-hydroxy-N-(1-benzo[b]thien-2-ylethyl) urea potassium salt
N-hydroxy-N-(1-benzo[b]thien-2-ylethyl) acetamide ammonium salt
N-hydroxy-N-(1-benzo[b]thien-2-ylethyl) acetamide triethyl ammonium salt
N-hydroxy-N-(1-benzo[b]thien-2-ylethyl) acetamide tetraethyl ammonium salt
N-butyryloxy-N-(1-benzo[b]thien-2-ylethyl) urea
N-benzoyloxy-N-(1-benzo[b]thienylethyl) urea The term "alkylene" is used herein to mean straight or branched chain spacer radicals such as —CH$_2$—, —CHCH$_3$—, —C(CH$_3$)$_2$—, —CH(C$_2$H$_5$)—, —CH$_2$CH$_2$—, —CH$_2$CHCH$_3$—, C(CH$_3$)$_2$C(CH$_3$)$_2$—, CH$_2$CH$_2$CH$_2$ and the like.

The term "alkenylene" is used herein to mean straight or branched chain unsaturated spacer radicals such as —CH=CH—, —CH=CHCH$_2$—, CH=CHCH(CH$_3$)—, —C(CH$_3$)=CHCH$_2$—, —CH$_2$CH=CHCH$_2$—, C(CH$_3$)$_2$CH=CHC(CH$_3$)$_2$—, and the like.

The term "alkyl" is used herein to mean straight or branched chain radicals of 1 to 12 carbon atoms, including, but not limited to methyl, ethyl, npropyl, isopropyl, n-butyl, sec-butyl, isobutyl, tert-butyl, and the like.

The term "alkenyl" is used herein to mean straight or branched chain unsaturated radicals of 2 to 12 carbon atoms, including, but not limited to ethenyl, 1-propenyl, 2-propenyl, 2-methyl-1-propenyl, 1-butenyl, 2-butenyl, and the like.

The term "cycloalkyl" is used herein to mean cyclic radicals, preferably of 3 to 8 carbons, including, but not limited to cyclopropyl, cyclobutyl, cyclopentyl, cyclohexyl, and the like.

The term "alkoxy" is used herein to mean —OR$_8$ wherein R$_8$ is an alkyl radical, including, but not limited to methoxy, ethoxy, isopropoxy, n-butoxy, secbutoxy, isobutoxy, tert-butoxy, and the like.

The term "thioalkyl" is used herein to mean —SR$_9$ wherein R$_9$ is an alkyl radical, including, but not limited to thiomethyl, thioethyl, thioisopropyl, n-thiobutyl, sec-thiobutyl, isothiobutyl, tert-thiobutyl, and the like.

The term "alkoyl" is used herein to mean —COR$_{10}$ wherein R$_{10}$ is an alkyl radical, including, but not limited to formyl, acetyl, propionyl, butyryl, isobutyryl, pivaloyl, and the like.

The term "carboalkoxy" is used herein to mean —COR$_{11}$ wherein R$_{11}$ is an alkoxy radical, including, but not limited to carbomethoxy, carboethoxy, carboisopropoxy, carbobutoxy, carbosec-butoxy, carboisobutoxy, carbotert-butoxy, and the like.

The term "aryl" is used herein to mean substituted and unsubstituted carbocyclic and heterocyclic aromatic radicals wherein the substituents are chosen from halo, nitro, cyano, C$_1$ to C$_{12}$ alkyl, alkoxy, and halosubstituted alkyl, including, but not limited to phenyl, 1- or 2-naphthyl, 2-, 3-, or 4-pyridyl, 2-, 3-furyl and the like.

The term "aroyl" is used herein to mean —COR$_{12}$ wherein R$_{12}$ is an aryl radical, including, but not limited to benzoyl, 1-naphthoyl, 2-naphthoyl, and the like.

The term "aryloxy" is used herein to mean —OR$_{13}$ wherein R$_{13}$ is an aryl radical, including, but not limited to phenoxy, 1-naphthoxy, 2-naphthoxy and the like.

The term "arylalkoxy" is used herein to mean —OR$_{14}$ wherein R$_{14}$ is an arylalkyl radical, including, but not limited to phenylmethoxy (i.e., benzyloxy), 4-fluorobenzyloxy, 1-phenylethoxy, 2-phenylethoxy, diphenylmethoxy, 1-naphthylmethoxy, 2-napthylmethoxy, 9-fluorenoxy, 2-, 3- or 4-pyridylmethoxy, 2-, 3-, 4-, 5-, 6-, 7-, 8-quinolylmethoxy and the like.

The term "arylthioalkoxy" is used herein to mean —SR$_{15}$ wherein R$_{15}$ is an arylalkyl radical, including, but not limited to phenylthiomethoxy (i.e., thiobenzyloxy), 4-fluorothiobenzyloxy, 1-phenylthioethoxy, 2-phenylthioethoxy, diphenylthiomethoxy, 1-naphthylthiomethoxy and the like.

The term "arylalkyl" is used herein to mean an aryl group appended to an alkyl radical, including, but not limited to phenylmethyl (benzyl), 1-phenylethyl, 2-phenylethyl, 1-naphthylethyl, 2-pyridylmethyl and the like.

The term "arylalkenyl" is used herein to mean an aryl group appended to an alkenyl radical, including, but not limited to phenylethenyl, 3-phenylprop-1-enyl, 3-phenylprop-2-enyl, 1-naphthylethenyl and the like.

The term "alkylsulfonyl" is used herein to mean —SO$_2$R$_{16}$ wherein R$_{16}$ is an alkyl radical, including, but not limited to methylsulfonyl (i.e. mesityl), ethyl sulfonyl, isopropylsulfonyl and the like.

The terms "halo" and "halogen" are used herein to mean radicals derived from the elements fluorine, chlorine, bromine, or iodine.

The term "halosubstituted alkyl" refers to an alkyl radical as described above substituted with one or more halogens, including, but not limited to chloromethyl, trifluoromethyl, 2,2,2-trichloroethyl, and the like.

The term "pharmaceutically acceptable cation" refers to non-toxic cations including but not limited to cations based on the alkali and alkaline earth metals, such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "lipoxygenase" is used herein to mean 5- and/or 12-lipoxygenase, the enzymes which oxidize arachidonic acid at the 5 and 12 prositions, respectively.

Method of Treatment

The compounds of the invention inhibit lipoxygenase activity, which makes the compounds useful in the treatment and prevention of disease states in which lipoxygenase may be involved, including, but not limited to, asthma, rheumatoid arthritis, gout, psoriasis, allergic rhinitis, adult respiratory distress syndrome, Crohn's disease, endotoxin shock, inflammatory bowel disease and/or ischemia induced myocardial or brain injury. In some cases this will involve preventing the underlying cause of the disease state and in other cases, while the underlying disease will not be affected the compounds of this invention will have the benefit of ameliorating the symptoms or preventing the manifestations of the disease.

Accordinglyhis invention also provides a method of treatment for inhibiting 5- and/or 12-lipoxygenase activity in a human or lower animal host in need of such treatment which method comprises administration to the human or lower animal host of a compound of the invention in a therapeutically effective amount to inhibit lipoxygenase activity in the host. This invention also provides a method of treating asthma, rheumatoid arthritis, gout, psoriasis, allergic rhinitis, adult respiratory distress syndrome, Crohn's disease, endotoxin shock, inflammatory bowel disease and/or ischemia induced myocardial or brain injury in a human or lower animal in need of such treatment comprising administering to the human or lower animal a therapeutically effective amount of a compound described above. Further, this invention also provides a method of treating or preventing the symptoms of the disease states mentioned above.

The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intra-arterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.1 to 20 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Formulation of Pharmaceutical Composition

This invention also provides pharmaceutical compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol.

Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipient such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

Synthesis of the Compounds

Several synthetic methods may be used to prepare compounds of this invention. Some of these methods are described by schemes 1-6 below. Although in each case the sequence is illustrated with a compound of formula I wherein $R_1$ is methyl or $NH_2$, A is —CHCH$_3$—, X is sulfur, Y is hydrogen, and Z is oxygen, it will be seen from the examples that other compounds of this invention can be prepared in the same manner using the appropriate starting materials. Compounds of formula I wherein $R_1$ is alkyl, alkenyl, N(alkyl)$_2$ or hydrogen may be prepared as described in scheme 1.

Scheme 1

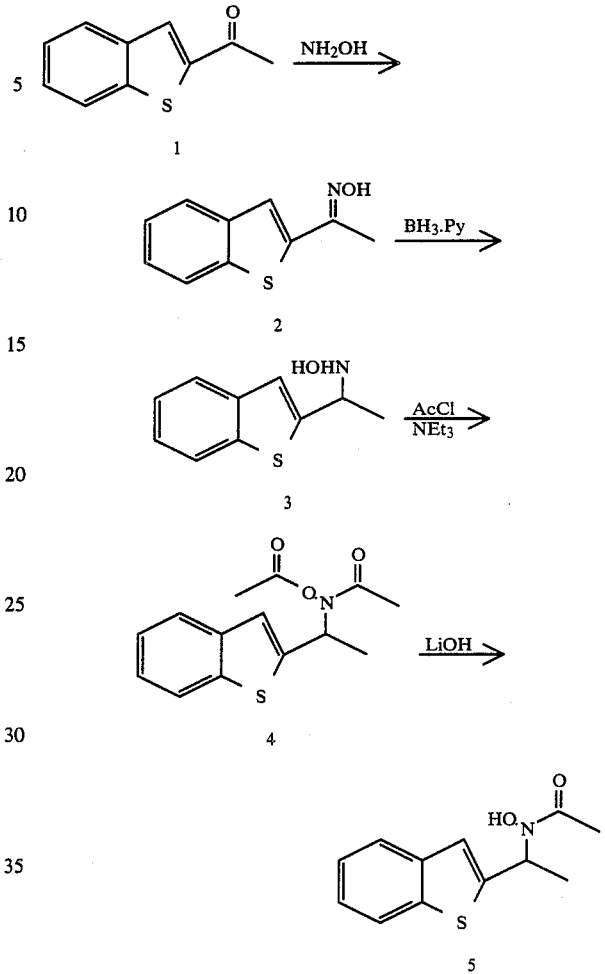

In scheme 1, 2-acetyl benzo[b]thiophene, 1 is treated with hydroxylamine in ethanol/pyridine to produce the oxime 2. This is reduced to the hydroxylamine 3 with borane pyridine complex and then converted to the N,O-diacetate 4 with acetyl chloride and triethylamine. The diacetate is converted to the hydroxamic acid 5 by hydrolysis with lithium hydroxide.

Other reagents may also be used to carry out the same transformation. For example 2 may be converted to 3 using borane trimethyl amine, borane-tetrahydrofuran, or other borane complexes. Intermediate 2 may also be converted to 3 with sodium cyanoborohydride or with phenyldimethylsilane in trifluoroacetic acid. Hydroxylamine 3 can also be converted to 4 with acylating agents such as acetic anhydride in the presence of other bases such as pyridine.

Compounds of formula I wherein $R_1$ is $NR_2R_3$ can be prepared according to the method outlined in scheme 2, below.

Scheme 2

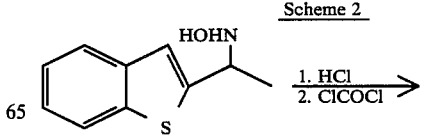

Hydroxylamine 3 is treated with trimethylsilyl isocyanate (TMSNCO), followed by ammonium chloride workup to give the urea 7. Alternatively, 3 can be treated with sodium or potassium cyanate in an acidic solution to yield the urea 7.

In addition to the methods described above, hydroxylamines such as 3 can be prepared as shown in scheme 4, below.

Hydroxylamine 3, the synthesis of which was described above, is treated with gaseous HCl followed by phosgene. The resulting putative carbamoyl chloride 6 is reacted without isolation with aqueous ammonia to yield the urea 7.

Compounds of formula I, wherein $R_1$ is $NR_2R_3$ and wherein at least one of either $R_2$ or $R_3$ is hydrogen can also be prepared according to Scheme 3, below.

Chloride 8 is treated with Z-furfuraldehyde oxime and a base such as sodium methoxide to give nitrone 9. The nitrone is then hydrolyzed under acidic conditions or with hydroxylamine. The hydroxyl amine can be converted to compounds such as 5 and 7 using the methodology described above. Compounds with other leaving groups including bromides, iodides, tosylates, mesylates, triflates can be used instead of chloride 8.

In addition to the methods described above, compounds of this invention may also be prepared as described in scheme 5, below.

Scheme 5

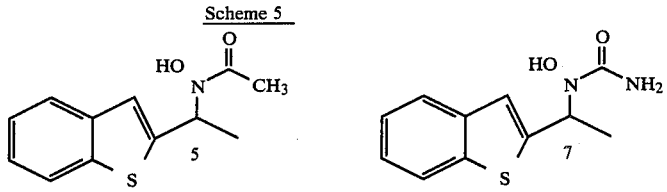

Chloride 8 is heated with O-benzylhydroxylamine in a solvent such as dimethylsulfoxide or tetrahydrofuran to yield the new hydroxylamine 10. This can either be reacted with acetyl chloride as in Scheme 1 to yield 11 or with trimethylsilyl isocyanate as in scheme 3 to yield 12. Compounds 11 and 12 are then hydrogenated to yield 5 and 7 respectively. In addition 11 and 12 may converted to 5 and 7 by treatment with ethane thiol in the presence of aluminum trichloride.

Other O-protected hydroxylamines may also be used in place of O-benzylhydroxylamine such as O-tetrahydropyranyl hydroxylamine. Further, other methods may be used to convert 10 to 7, such as treatment with phosgene followed by ammonium hydroxide such as described in scheme 2, or treatment with sodium cyanate as described in Scheme 3.

Compounds of this invention in which A is —$CH_2$— or —CH(alkyl)— may also be prepared as described in Scheme 6.

Scheme 6

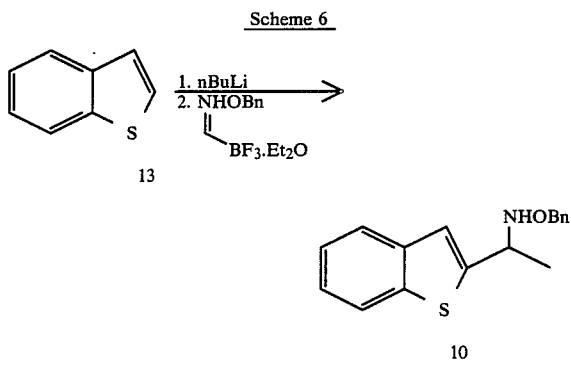

Benzo[b]thiophene 13 is first converted to 2-lithiobenzo[b]thiophene by treatment with n-butyllithium. This is then treated with the O-benzyloxime of acetaldehyde in the presence of $BF_3.Et_2O$ to give O-benzylhydroxylamine 10. This may be converted to the compounds such as 5 or 7 as described in scheme 4. Other O-protected oximes can be substituted for the O-benzyl oxime.

The following examples further illustrate the synthesis and use of compounds of this invention. The appropriate designations for $R_1$, A, X and Y as defined by formula I are given for each example below. Unless otherwise noted, Z is oxygen and M is hydrogen.

EXAMPLE 1

N-hydroxy-N-(1-benzo[b]thien-2-ylethyl) acetamide a. 2-Acetyl benzo[b]thiophene. Method a. Using the method described in Scheme 1, benzo[b]thiophene (10 g, 75 mmole) was dissolved in THF (50 mL) and cooled to −78° C. Butyl lithium (28 mL, 2.7 M in hexanes) was added. The mixture was stirred for 15 minutes and N,O-dimethyl acetohydroxamic acid was added. Following an additional 30 minutes of stirring, the reaction was quenched at −78° C. with ethanol and 2N HCl solution and extracted into ether. The solvent was removed in vacuo and the residue chromatographed on silica gel eluting with 20% ether in pentane to yield 6.9 g of the desired product as a white solid.

Method b. To a solution of benzo[b]thiophene (10.0 g, 75 mmole) in THF (50 mL) was added n-butyl lithium (33 mL, 2.5M in hexanes) at −70° C. under $N_2$. The mixture, containing a white precipitate, was stirred at −70° C. for 1 hour. Acetaldehyde (4.6 mL, 82 mmole) was added dropwise. After a few minutes the reaction was quenched with saturated $NH_4Cl$ solution. The layers were separated, the organic layer dried over $MgSO_4$, filtered, and evaporated to give a white solid (10 g) which was used directly for the next step.

The alcohol prepared as described above (1.0 g) in acetone (50 mL) was cooled to 5° C. and Jones Reagent was added dropwise until the orange yellow color persisted (1.4 mL). The reaction mixture was diluted with water and the desired product precipitated. It was collected by filtration to give 0.85 g.

b. 2-Acetyl benzo[b]thiophene oxime. 2-Acetyl benzo[b]thiophene (5 g, 28.4 mmole), prepared as described in step a above, and hydroxylamine hydrochloride (3.0 g, 42.6 mmole) were dissolved in a mixture of ethanol (50 mL) and pyridine (50 mL) and allowed to stir at room temperature for 2 hours. Most of the solvent was removed in vacuo and the residue dissolved in ether. After washing with 2N HCl (100 mL), the solution was dried over $MgSO_4$ and evaporated. A white crystalline solid was obtained and was carried on without further purification.

An alternative work-up may also be used. The reaction mixture was diluted with water (300 mL) and the product precipitated. It was filtered off and dried in vacuo.

c. 1-Benzo[b]thien-2-ylethyl hydroxylamine. The oxime prepared as in step b above (3.5 g, 18.5 mmole) was dissolved in ethanol (25 mL) and cooled to 0° C. Borane pyridine complex (3.7 mL, 37 mmole) was added via syringe under nitrogen followed ten minutes later by 20% HCl in ethanol (30 mL). Within thirty minutes the reaction was complete and was brought to pH 9 with the addition of solid sodium carbonate or 2N NaOH. The mixture was extracted into ether and dried over $MgSO_4$. After evaporation a white solid (3.0 g) was obtained. This was carried on without further purification.

d. N-Acetoxy-N-(1-benzo[b]thien-2-ylethyl) acetamide. The hydroxylamine (1.0 g, 5.2 mmole) prepared as in step c above and pyridine (1.0 mL, 13 mmole) were dissolved in tetrahydrofuran (40 mL) and cooled to 0° C. Acetyl chloride (1.0 mL, 13 mmole) was added slowly. After stirring for 30 minutes the reaction mixture was washed with 2N HCl, dried over $MgSO_4$ and evaporated.

e. N-hydroxy-N-(1-benzo[b]thien-2-ylethyl) acetamide. The material obtained in the previous step (1.0 g)

was dissolved in isopropyl alcohol (10 mL) and lithium hydroxide (1.0 g) in water (10 mL). After stirring for thirty minutes, most of the solvent was removed in vacuo. The residue was neutralized with 2N HCl, extracted with ether, and the organic phase was then dried over MgSO$_4$ and evaporated. The desired product was obtained as a white crystalline solid (750 mg) following silica gel chromatography. (R$_1$=CH$_3$, A=CHCH$_3$, X=S, Y=H).

Melting Point: 108–110° C.

NMR (300 MHz, DMSO-d$_6$): 1.56 (d, 3H); 2.02 (s, 3H); 5.90 (m, 1H); 7.29–7.38 (m, 3H); 7.75–7.92 (m, 2H); 9.75 (brs, 1H).

Mass spectrum (EI):235 M+,218, 176, 161, 128.

EXAMPLE 2

N-hydroxy-N-(1-benzo[b]thien-2-ylethyl) urea

Method a. Using the method of Scheme 3, 1-benzo[b]thien -2-yl ethyl hydroxyl amine prepared as described in example 1, step c (2.0 g, 10 mmole), was refluxed for thirty minutes with trimethylsilyl isocyanate (1.65, 14.2 mmole) in dioxane (30 mL). The reaction mixture was then washed with saturated NH$_4$C 1 solution, dried with MgSO$_4$, and evaporated.

Method b. Using the method of Scheme 2, 1-benzo[b]thien -2-yl ethyl hydroxyl amine prepared as described in example 1, step c, was dissolved in toluene (100 mL) and HCl gas was bubbled through the mixture at a moderate rate for about four minutes. The solution was then heated to reflux and phosgene was bubbled through for another four minutes. After an additional one hour reflux, the mixture was allowed to cool to room temperature and then added to excess cold ammonium hydroxide solution. The precipitate was collected and recrystallized. (R$_1$=NH$_2$, A=CHCH$_3$, X=S [2-isomer], Y=H)

Melting Point: 157°–158° C.

NMR (300 MHz, DMSO-d$_6$): 1.51 (d, 3H); 5.55 (q, 1H); 6.45 (brs, 2H), 7.25–7.37 (m, 3H); 7.75–7.91 (m, 2H); 9.35 (s, 1H).

Mass spectrum (CI–NH$_3$): 237 (M+1)+, 221, 194, 176, 161.

EXAMPLE 3

N-hydroxy-N-(1-benzo[b]thien-2-ylethyl) N'-methyl urea

The desired compound was prepared according to the method of example 2, method a, except using methyl isocyanate instead of trimethylsilyl isocyanate. (R$_1$=NHCH$_3$, A=CHCH$_3$, X=S[2-isomer], Y=H)

Melting Point: 149°–150° C.

NMR (300 MHz, DMSO-d$_6$): 1.51 (d, 3H, J=7.5 Hz); 2.60 (d, 3H); 5.55 (q, 1H, J=7.5 Hz); 6.98 (m, 1H); 7.24–7.37 (m, 3H); 7.73–7.79 (m, 1H); 7.85–7.91 (m, 1H); 9.17 (s, 1H).

Mass Spectrum (CI–NH$_3$): 251 (M+H)+,268 (N+NH$_3$)+

EXAMPLE 4

N-hydroxy-N-(1-benzo[b]thien-2-ylethyl) N', N'-dimethyl urea

The desired compound was prepared according to the method of example 1, except using dimethylcarbamoyl chloride instead of acetyl chloride. (R$_1$=N(CH$_3$)$_2$, A=CHCH$_3$, X=S [2-isomer], Y=H).

Melting Point: 139°–141° C.

NMR (300 MHz, DMSO-d$_6$): 1.54 (d, 3H, J=7.5 Hz); 2.87 (s, 6H); 5.24 (q, 1H); 7.25–7.37 (m, 3H); 7.74–7.79 (m, 1H); 7.85–7.91 (m, 1H); 8.92 (s, 1H).

Mass Spectrum (CI-NH$_3$): 264 (M+H)+,282 (M+NH$_4$)+

EXAMPLE 5

N-hydroxy-N-benzo[b]thien-2-ylmethyl urea

The desired compound was prepared according to the method of example 1, except using dimethyl formamide instead of N,O-dimethyl acetohydroxamic acid. (R$_1$=NH$_2$, A=CH$_2$, X=S [2-isomer], Y=H).

Melting Point: 170.5°–172° C.

NMR (300 MHz, DMSO-d$_6$): 4.74 (s, 2H); 6.47 (brs, 2H); 7.23 (m, 2H); 7.78 (m, 1H); 7.90 (m, 1H); 9.53 (s, 1H).

Mass spectrum (CI-NH$_3$): 223 (M+H)+, 240 (M+NH$_4$)+

EXAMPLE 6

N-hydroxy-N-benzo[b]thien-2-ylmethyl N'-methyl urea

The desired compound was prepared according to the method of example 1, except using dimethyl formamide instead of N,O-dimethyl acetohydroxamic acid and using methyl isocyanate instead of trimethylsilyl isocyanate. (R$_1$=NHCH$_3$, A=CH$_2$, X=S [2-isomer], Y=H).

Melting Point: 160°–161° C.

NMR (300 MHz, DMSO-d$_6$): 2.61 (d, 3H); 4.74 (s, 2H); 7.01 (q, 1H); 7.26–7.38 (m, 3H); 7.74–7.97 (m, 2H); 9.46 (s, 1H).

Mass Spectrum (CI-NH$_3$): 237 (M+H)+,254 (M+NH$_4$)+

EXAMPLE 7

N-hydroxy-N-benzo[b]thien-2-ylmethyl N',N'-dimethyl urea

The desired compound was prepared according to the method of example 1, except using dimethyl formamide instead of N,O-dimethyl acetohydroxamic acid and using dimethylcarbamoyl chloride instead of acetyl chloride. (R$_1$=N(CH$_3$)$_2$, A=CH$_2$, X=S [2-isomer], Y=H).

Melting Point: 145°–147° C.

NMR (300 MHz, DMSO-d$_6$): 2.88 (s, 6H); 459 (s, 2H); 7.26–7.37 (m, 3H); 7.74–7.80 (m, 1H); 7.87–7.93 (m, 1H); 9.31 (s, 1H).

Mass Spectrum (CI-NH$_3$): 250 (M+H)+,268 (M+NH$_4$)+

EXAMPLE 8

N-hydroxy-N-(1-benzo[b]thien-3-ylethyl) acetamide a. 3-Acetyl benzothiophene. A solution of benzothiophene (20 g, 149 mmole) in nitroethane (100 mL) was added to a solution of AlCl$_3$ (59.7 g, 448 mmole) and acetyl chloride (10.6 mL, 149 mmole) in nitroethane (150 mL) at 0° C. The ice bath was removed after the addition was complete and the mixture was allowed to stir for 15 hours at room temperature. The mixture was poured onto ice (500 mL) and concentrated HCl(150 mL). The desired material was extracted into ethyl acetate which was dried over MgSO$_4$. The dark brown oil which resulted was chromatographed on silica gel eluting with 10% ethyl acetate in hexanes to give the desired material (3.8 g).

b. N-hydroxy-N-(1-benzo[b]thien-3-yl)ethyl acetamide was prepared using the methods of example 1, steps b-e, except using the 3-acetyl benzo[b]thiophene instead of 2-acetylbenzo[b]thiophene. ($R_1$=CH$_3$, A=CHCH$_3$, X=S [3-isomer], Y=H).

Melting Point: 123°–125° C.

NMR (300 MHz, DMSO-d$_6$): 1.57 (d, 3H); 2.00 (brs, 3H); 6.03 (q, 1H); 7.32–7.44 (m, 2H); 7.71 (s, 1H); 7.80–8.02 (m, 2H); 9.45 (brs, 1H).

Mass Spectrum (CI-NH$_3$): 236 (M+H)$^+$, 253 (M+NH$_4$)$^+$.

EXAMPLE 9

N-hydroxy-N-(1-benzo[b]thien-3-ylethyl) urea

The desired material was prepared according to the method of example 2, except using 3-acetyl benzo[b]thiophene instead of 2-acetyl benzo[b]thiophene. ($R_1$=NH$_2$, A=CHCH$_3$, X=S [3-isomer], Y=H).

Melting Point: 180° C. dec.

NMR (300 MHz, DMSO-d$_6$): 1.50 (d, 3H); 5.73 (q, 1H); 6.35 (br s, 2H); 7.30–7.43 (m, 2H); 7.67 (s, 1H); 7.90–8.00 (m, 2H); 8.96 (s, 1H).

Mass Spectrum (EI): 236 M$^+$, 219, 161, 128.

EXAMPLE 10

N-hydroxy-N-[1-(3-methylbenzo[b]thien-2-yl)ethyl]urea

The desired compound was prepared according to the method of example 2, except using 3-methylbenzothiophene instead of benzothiophene. ($R_1$=NH$_2$, A=CHCH$_3$, X=S[2-isomer], Y=3—CH$_3$).

Melting Point: 130°–132° C.

NMR (300 MHz, DMSO-d$_6$): 1.57 (d, 3H); 2.00 (br s, 3H); 6.03 (q, 1H); 7.32–7.44 (m, 2H); 7.71 (s, 1H); 7.80–8.02 (m, 2H); 9.45 (br s, 1H).

Mass Spectrum (CI-NH$_3$): 236 (M+H)$^+$, 253 (M+NH$_4$)$^+$

EXAMPLE 11

N-hydroxy-N-[1-(5-(2,2-dimethylethyl)benzo[b]thien-3-yl)ethyl]urea a. 4-t-Butyl thiophenol. 4-t-Butyl bromo benzene (10 g, 47 mmole) in ether (100 mL) was heated at reflux for 2 hours in the presence of magnesium metal (1.2 g, 49 mmole). When the Grignard reagent had formed the mixture was cooled to 0° C. and sulfur (1.5 g) was added in portions over 10 minutes. The ice bath was removed and the reaction mixture was stirred at room temperature for 1 hour. The mixture was poured into ice water, acidified with 10% HCl and extracted into ether. The organic layer was washed with saturated sodium chloride and dried over MgSO$_4$. The solvent was evaporated to give a cloudy yellow liquid (8.1 g) which was carried on as is.

b. 4-t-Butylphenyl-2-thiapropionaldehyde diethyl acetal. A solution of the thiophenol (prepared as described above, 8.1 g) in THF (25 mL) was added dropwise to a suspension of sodium hydride (2.0 g, 60%, prewashed with hexanes) in THF (50 mL). The mixture was stirred for 30 minutes and then bromo acetaldehyde diethyl acetal (9.3 g, 47 mmole) in ether (25 mL) was added. This mixture was stirred overnight at room temperature. NH$_4$Cl was added and the solvent was removed in vacuo. The residue was partitioned between ether and water. The organic layer was dried over MgSO$_4$ and concentrated. The residue was vacuum distilled to give a yellow oil (5.9 g), bp 142° C./1 mm.

c. 5-t-Butylbenzothiophene. Phosphorous pentoxide and phosphoric acid were combined and heated at 130°–135° for 45 minutes. The temperature was raised to 175° and the acetal prepared as in step b above (6.2 g, 2.2 mmole) was added dropwise. The hot solution was dumped onto ice and extracted three times with ether. The combined organic layers were dried over MgSO$_4$ and concentrated to give a brown oil. This oil was filtered through a pad of silica gel, flushed with hexanes. A clear yellow liquid was obtained (2.26 g).

d. N-hydroxy-N-[1-(5-(2,2-dimethylethyl)benzo[b]-thien-2-yl)-ethyl]urea. The desired compound was prepared according to the method of example 2, except using the material prepared as in step c, above, instead of benzothiophene. ($R_1$=NH$_2$, A=CHCH$_3$, X=S[2-isomer], Y=5—(CH$_3$)$_3$C).

Melting Point: 151°–153° C.

NMR (300 MHz, DMSO-d$_6$): 134 (s, 9H); 1.50 (d, 3H); 5.55 (q, 1H); 6.44 (brs, 2H); 7.22 (s, 1H); 7.37 (dd, 1H); 7.74 (d, 1H); 7.77 (d, 1H); 9.21 (brs, 1H).

Mass Spectrum (CI-NH$_3$): 293 (M+H)$^+$, 310 (M+NH$_4$)$^+$, 217.

EXAMPLE 12

N-hydroxy-N-[1-benzo[b]thien-2-ylethyl) acetamide 1,1-dioxide a. N-acetoxy-N-(1-benzo[b]thien-2-ylethyl) acetamide dioxide.

Peracetic acid (1.64 g, 8.6 mmole) in acetic acid (5 mL) was added to a solution of N-acetoxy-N-(1-benzo[b]thien-2-ylethyl acetamide (0.71 g, 2.6 mL), prepared as described in example 1, in acetic acid at 0° C. The mixture was stirred overnight and then poured into saturated aqueous sodium bicarbonate. The aqueous layer was extracted twice with ethyl acetate. The combined organic layers were dried over MgSO$_4$ and concentrated. The residue was chromatographed on 50 g silica gel eluting with 50% ethyl acetate in chloroform. The desired product was obtained as a white foam (0.58 g).

b. N-hydroxy-N-(1-benzo[b]thien-2ylethyl) acetamide dioxide was prepared using the procedure of example 1, step e, except using the material prepared as in step a above instead of N-acetoxy-N-(1-benzo[b]thien-2-ylethyl) acetamide. ($R_1$=CH$_3$, A=CHCH$_3$, X=SO$_2$[2-isomer], Y=H).

Melting Point: 151°–157° C.

NMR (300 MHz, DMSO-d$_6$): 1.47 (d, 3H); 2.04 (s, 3H); 5.62 (m, 1H); 7.45 (s, 1H); 7.60 (m, 2H); 7.69 (m, 1H); 7.84 (d, 1H); 9.83 (br s, 1H).

Mass Spectrum (CI-NH$_3$): 268 (M+H)$^+$, 252.

EXAMPLE 13

N-hydroxy-N-(1-benzo[b]thien-2-ylethyl)urea 1,1-dioxide

The desired material was prepared using the procedure of example 12, step a, except using N-hydroxy-N-(1-benzo[b]thien-2-ylethyl) urea instead of N-acetoxy-N-(1-benzo[b]thien-2-ylethyl) acetamide. ($R_1$=NH$_2$, $R_2$=CH$_3$, X=SO$_2$[2-isomer], Y=H).

NMR (300 MHz, DMSO-d$_6$): 1.42 (d, 3H); 5.29 (m, 2H); 6.57 (brs, 2H); 7.38 (s, 1H); 7.58 (m, 2H); 7.67 (m, 1H); 7.84 (d, 1H); 9.36 (s, 1H).

EXAMPLE 14

N-hydroxy-N-(1-benzo[b]fur-2-ylethyl) acetamide

The desired compound was prepared according to the method of example 1, except using benzo[b]furan instead of benzo[b]thiophene ($R_1$=CH$_3$, A=CHCH$_3$, X=O[2-isomer], Y=H)

Melting Point: 130°–132° C.

NMR (300 MHz, DMSO-$d_6$): 1.44 (d, 3H); 2.36 (s, 3H); 5.77 (q, 1H); 6.37 (br s, 2H); 7.28–7.40 (m, 2H); 7.68–7.73 (m, 1H); 7.88–7.90 (m, 1H); 9.33 (s, 1H).

Mass spectrum (CI−NH$_3$): 222 (M+H)$^+$, 239 (M+NH$_4$)$^+$

EXAMPLE 15

N-hydroxy-N-(1-benzo[b]fur-2-ylethyl) urea

The desired compound was prepared according to the method of example 2, except using benzo[b]furan instead of benzo[b]thiophene ($R_1$=NH$_2$, A=CHCH$_3$, X=O[2-isomer], Y=H)

Melting Point: 147°–150° C.

NMR (300 MHz, DMSO-$d_6$): 1.46 (d, 3H); 5.47 (q, 1H); 6.48 (brs, 2H); 7.22 (m, 2H); 7.50 (d, 1H); 7.58 (m, 1H); 9.18 (s, 1H).

Mass spectrum (CI−NH$_3$): 221 (M+H)$^+$, 238 (M+NH$_4$)$^+$, 205, 145.

EXAMPLE 16

N-hydroxy-N-(1-(1-methylindol-3-yl)ethyl) acetamide a. 1-Methyl-2-acetyl indole. 2-Acetyl indole (15 g, 0.94 mmole) and sodium hydroxide (32 g) were dissolved in water (300 mL). Dimethyl sulfate (67.5 g) was added and the mixture was heated at 85° for 4 hours. The reaction mixture was then cooled and filtered to collect the product.

b. N-hydroxy-N-(1(1-methylindol-3-yl)ethyl) acetamide was prepared according to the method of example 1, steps b-e, except using the material prepared as in step a above instead of 2-acetyl benzothiophene. ($R_1$=CH$_3$, A=CHCH$_3$, X=NCH$_3$[3-isomer], Y=H).

Melting Point: 106.5°–108° C.

NMR (300 MHz, DMSO-$d_6$): 1.52 (d, 3H); 1.96 (s, 3H); 5.96 (m, 1H); 7.00 (m, 1H); 7.32 (s, 1H); 7.32 (d, 1H); 7.55 (d, 1H); 9.39 (br s, 1H).

Mass spectrum (EI): 232 M$^+$, 215, 158.

EXAMPLE 17

N-hydroxy-N-(1-(1-methylindol-3-yl)ethyl) urea

The desired compound was prepared using the method of example 2, except using 1-methyl-3-acetyl indole, prepared as described in example 16, step a instead of acetyl benzo[b]thiophene. ($R_1$=NH$_2$, A=CHCH$_3$, X=NCH$_3$[3-isomer], Y=H).

Melting Point: 149°–150° C.

NMR (300 MHz, DMSO-$d_6$): 1.46 (d, 3H, J=7.5 Hz); 3.74 (s, 3H); 5.66 (q, 1H); 6.18 (br s, 2H); 6.94–7.15 (m, 2H); 7.24 (s, 1H); 7.36 (m, 1H); 7.64 (m, 1H); 8.88 (s, 1H).

Mass Spectrum (CI−NH$_3$): 234 (M+H)$^+$, 251 (M+NH$_4$)$^+$, 158.

EXAMPLE 18

N-hydroxy-N-(1-(1-methylindol-3-yl)ethyl)N'-methyl urea

The desired compound was prepared using the method of example 2, except using 1-methyl-3-acetyl indole, prepared as described in example 16, step a instead of acetyl benzo[b]thiophene and using methyl isocyanate instead of trimethylsilyl isocyanate. ($R_1$=NHCH$_3$, A=CHCH$_3$, X=NCH$_3$[3-isomer], Y=H).

Melting Point: 152°–153° C.

NMR (300 MHz, DMSO-$d_6$): 1.45 (d, 3H, J=7.5 Hz); 2.57 (d, 3H); 3.73 (s, 3H); 5.58 (q, 1H); 6.71 (brs, 2H); 6.94–7.15 (m, 2H); 7.24 (s, 1H); 7.35 (m, 1H); 7.62 (m, 1H); 8.74 (s, 1H).

Mass Spectrum (CI−NH$_3$): 248 (M+H)$^+$, 265 (M+NH$_4$)$^+$, 158.

EXAMPLE 19

N-hydroxy-N-(1-benzo[b]thien-2-ylethyl) urea sodium salt

Sodium bistrimethyl silyl amide (10.8 mL, 1.0 M in THF) was added to a solution of N-hydroxy-N-(1-benzo[b]thien-2-ylethyl) urea (2.5 g, 10.5 mmole), prepared as described in example 2, in THF (50 mL. Hexanes (50 mL) was added and a precipitate formed. The material was collected by filtration and washed with hexanes and ether. After drying in vacuo a white solid (1.5 g) was obtained. ($R_1$=NH$_2$, A=CHCH$_3$, X=S[2-isomer], Y=H, M=Na).

NMR (300 MHz, DMSO-$d_6$): 1.51 (d, 3H); 2.02 (s, 2H); 4.28, 5.65 (q, 1H); 7.10–7.32 (m, 3H); 7.58–7.75 (m, 2H).

EXAMPLE 20

N-hydroxy-N-(1-benzo[b]thien-2-ylethyl) formamide

The desired compound was prepared according to the method of example 1, except using acetyl formyl anhydride instead of acetyl chloride. ($R_1$=H, A=CHCH$_3$, X=S[2-isomer], Y=H).

Melting Point: 115°–116.5° C.

NMR (300 MHz, DMSO-$d_6$): 1.61 (s, 3H); 5.4,5.8 (br d, 1H); 7.3–7.4 (m, 3H); 7.77–7.95 (m, 2H); 8.23–8.36 (br d, 1H); 9.8 (br d, 1H).

IR (CHCl$_3$): 160, 2890.

Mass spectrum (CI−NH$_3$): 222 (M+H)$^+$, 239 (M+NH$_4$)$^+$, 195, 178.

Analysis: Calculated—C 59.71, H 5.01, N 6.33; Found—59.76; 5.00; 6.31.

EXAMPLE 21

N-hydroxy-N-(1-benzo[b]thien-2-ylethyl)2-methylpropionamide

The desired compound was prepared using the method of example 1, except using isobutyryl chloride instead of acetyl chloride. ($R_1$=(CH$_3$)$_2$CH, A=CHCH$_3$, X=S[2-isomer], Y=H).

Melting Point: 132°–138° C.

NMR (300 MHz, DMSO-$d_6$): 0.98 (d, 3H); 1.06 (d, 3H); 1.57 (d, 3H); 3.04 (m, 1H); 5.90 (q, 1H); 7.28–7.38 (m, 3H); 7.78–7.92 (m, 2H); 9.62 (s, 1H).

IR (CHCl$_3$): 1620, 2980.

Mass spectrum (CI−NH$_3$): 264 (M+H)$^+$, 281 (M+NH$_4$)$^+$, 195, 178.

EXAMPLE 22

N-hydroxy-N-[1-(5-chlorobenzo[b]fur-2-yl)ethyl]urea a. 2-Acetyl-5-chlorobenzo[b]furan. 5-Chloro salicylaldehyde (15.6 g, 100 mmole) was added to a suspension of potassium carbonate (17.3 g, 125 mmole) in acetone (100 mL). To this was added chloroacetone (90%, 12.0 g) in acetone 50 mL). The mixture was heated at reflux for 24 hours. After cooling, the acetone was removed by evaporation and the residue poured into ice water and 6N HCl. This was extracted with ethyl acetate, which was dried over Na$_2$SO$_4$ and concentrated in vacuo to give the desired material as a crystalline solid (8.24 g).

b. N-hydroxy-N-[1-(5-chlorobenzo[b]fur-2-yl)ethyl]urea was prepared using the method of example 2, except using the material prepared as in step a, above, instead of 2-acetylbenzothiophene. ($R_1$=$NH_2$, A=$CHCH_3$, X=O[2-isomer], Y=5-Cl).

Melting Point: 173.5°–175° C.

NMR (300 MHz, DMSO-$d_6$): 1.46 (d, 3H, J=7.0); 5.46 (q, 1H, J=7.0); 6.50 (brs, 2H); 6.73 (s, 1H); 7.27 (dd, 1H, J=8.8, J=2.2); 7.55 (d, 1H, J=8.8); 7.66 (d, 1H; J=2.2); 9.21 (s, 1H)

EXAMPLE 23

N-hydroxy-N-[1-(5-methoxybenzo[b]fur-2-yl)ethyl]urea

The desired material was prepared using the method of example 22 except using 4-methoxysalicylaldehyde instead of 4-chlorosalicylaldehyde. ($R_1$=$NH_2$, A=$CHCH_3$, X=O[2-isomer], Y=5-$CH_3O$).

Melting point: 149°–151° C.

NMR (300 MHz, DMSO-$d_6$): 1.44 (d, 3H, J=7.0); 3.76 (s, 3H); 5.43 (q, 1H, J=7.0); 6.47 (brs, 2H); 6.65 (m, 1H); 6.83 (dd, 1H, J=2.6, J=9.2); 7.08 (d, 1H, J=2.6); 7.39 (d, 1H, J=9.2); 9.17 (s, 1H).

EXAMPLE 24

N-hydroxy-N-(1-(1-methylindol-2-yl)ethyl)urea

The desired compound was prepared using the method of example 2, except using 1-methyl-2-acetyl indole, prepared as described in example 16, step a instead of acetyl benzo[b]thiophene. ($R_1$=$NH_2$, A=$CHCH_3$, X=$NCH_3$[2-isomer], Y=H).

Melting Point: 137°–139° C.

NMR (300 MHz, DMSO-$d_6$): 1.48 (d, 3H, J=7 Hz); 3.75 (s, 3H); 5.70 (q, 1H); 6.15 (br s, 2H); 6.70 (s, 1H); 6.94 (m, 1H); 7.15 (m, 1H); 7.35 (m, 1H); 7.65 (m, 1H); 8.90 (s, 1H).

IR: 3300, 1660, 1580.

Mass Spectrum (CI−$NH_3$): 234 (M+H)+, 251 (M+$NH_4$)+, 158.

EXAMPLE 25

N-hydroxy-N-(1-benzo[b]thien-2-ylethyl)thiourea

The desired compound was prepared according to the method of example 2, method a, except using trimethylsilyl isothiocyanate instead of trimethylsilyl isocyanate ($R_1$=$NH_2$, A=$CHCH_3$, X=S[2-isomer], Y=H, Z=S).

Melting Point: 165° C. dec.

NMR (300 MHz, DMSO-$d_6$): 1.58 (3, d, J=7.5 Hz); 6.83 (1, m); 7.26–7.37 (3, m); 7.53–7.62 (1, br s); 7.75–7.92 (2, m); 7.92–8.02 (1, br s); 9.28 (1, br s).

Mass spectrum (DCI−$NH_3$): 253 (M+H)+, 270 (M+$NH_4$)+, 237, 161.

Analysis ($C_{11}H_{12}N_2OS_2$): Calculated—C: 52.36, H: 4.79, N: 11.10; Found C: 52.60, H: 4.88, N: 11.04.

EXAMPLE 26

N-hydroxy-N-[1-(3-methoxybenzo[b]thien-2-yl)ethyl]urea a. 2-(2-Oxothiopropoxy)benzoic acid. Potassium carbonate (8.97 g, 64.9 mmole) was added to a solution of thiosalicylic acid (10 g, 65 mmole) in ethanol (70 mL). The mixture was heated at reflux for 3 hours and then the solvent was evaporated. The residue was dissolved in water and the solution acidified to pH 1 with concentrated HCl. The desired product precipitated and was collected and recrystallized from ethyl acetate/hexanes. Two crops were collected for a total of 10.2 g (81%) of the desired product.

b. Methyl 2-(2-oxothiopropoxy)benzoic acid. The material prepared as described in step a, above (2.0 g, 10.3 mmole) was suspended in ether and excess diazomethane in ether was added. The residual diazomethane was destroyed by the addition of aqueous HCl. The ether layer was dried over $MgSO_4$ and the solvent removed in vacuo to give the desired product (1.95 g, 85%).

c. 3-Hydroxy-2-acetylbenzo[b]thiophene. Sodium methoxide (230 mg, 4.3 mmole) was added to a solution of the ester prepared as in step b, above (1.9 g, 8.5 mmole) in methanol (40 mL). Chloroacetone (6.2 mL, 77 mmole) was added and the reaction mixture was heated at reflux for four hours and then allowed to stir for fifteen hours at room temperature. The solvent was removed in vacuo and the residue partitioned between 2N NaOH and ethyl acetate. The aqueous phase was acidified with concentrated HCl and the desired product precipitated. It was collected by filtration (1.9 g, 85%).

d. 3-Methoxy-2-acetylbenzo[b]thiophene. The material prepared as in step c was converted to the desired product by treatment with diazomethane using the procedure described in step b, above.

e. N-hydroxy-N-[1-(3-methoxybenzo[b]thien-2-yl)ethyl]urea was prepared according to the method of example 2, method a, except using the material prepared as in step d, above instead of 2-acetylbenzo[b]thiophene. ($R_1$=$NH_2$, A=$CHCH_3$, X=S[2-isomer], Y=3-$OCH_3$).

Melting Point: 158° C. dec.

NMR (300 MHz, DMSO-$d_6$): 1.42 (d, 3H, J=7.5 Hz); 3.91 (s, 3H); 5.81 (q, 1H, J=7.5 Hz); 6.42 (br s, 2H); 7.30–7.41 (m, 2H); 7.66–7.73 (m, 1H); 7.82–7.88 (m, 1H); 9.44 (s, 1H).

Mass spectrum (DCI−$NH_3$): 267 (M+H)+, 284 (M+$NH_4$)+.

Analysis ($C_{12}H_{14}N_2O_3S$): Calculated—C: 54.12, H: 5.30, N: 10.52; Found C: 54.11, H: 5.34, N: 10.27.

EXAMPLE 27

N-hydroxy-N-[1-(3-thioethylbenzo[b]thien-2-yl)ethyl]urea a. 1-(3-thioethoxybenzo[b]thien-2-yl)ethyl hydroxylamine. A solution of 1-(3-methoxybenzo[b]thien-2-yl)ethyl hydroxylamine (250 mg, 1.1 mmole), prepared as described in example 26 in methylene chloride (5 mL), was added to a solution of aluminum chloride (895 mg, 6.7 mmole) in ethanethiol (4 mL) at 0° C. The cold bath was removed and the mixture was allowed to stir for 3 hours. The mixture was poured onto ice and extracted into ethyl acetate. The organic layer was dried over $MgSO_4$ and evaporated to give the desired product as a yellow oil (250 mg).

b. N-hydroxy-N-[1-(3-thioethylbenzo[b]thien-2-yl)ethyl]urea. The desired product was obtained using the method of example 2, method a, except using the material prepared as in step a, above, instead of 1-(benzo[b]thien-2-yl)ethyl hydroxylamine ($R_1$=$NH_2$, A=$CHCH_3$, X=S[2-isomer], Y=3-$SC_2H_5$).

Melting Point: 153°–155° C.

NMR (300 MHz, DMSO-$d_6$): 1.10 (t, 3H, J=7.5 Hz); 1.44 (d, 3H, J=7.0 Hz); 2.70 (m, 2H); 6.18 (q, 1H, J=7.0

Hz); 6.45 (br s, 2H); 7.41 (m, 2H); 7.93 (m, 2H); 9.57 (s, 1H).

Mass spectrum (DCI—NH$_3$): 297 (M+H)$^+$, 314 (M+NH$_4$)$^+$, 221.

Analysis (C$_{13}$H$_{16}$N$_2$O$_2$S$_2$): Calculated—C: 52.68, H: 5.44, N: 9.45; Found C: 52.35, H: 5.41, N: 9.26.

EXAMPLE 28

N-hydroxy-N-[1-(4,7-dimethylbenzo[b]thien-2-yl)ethyl]urea

The desired compound was prepared according to the method of example 11 except using 2,5-dimethyl bromobenzene instead of 4-t-butylbromobenzene (R$_1$=NH$_2$, A=CHCH$_3$, X=S[2-isomer], Y=4,7-(CH$_3$)$_2$).

Melting Point: 149°–152° C.

NMR (300 MHz, DMSO-d$_6$): 1.52 (d, 3H, J=7.5 Hz); 2.42 (s, 3H); 2.50 (s, 3H); 5.60 (m, 1H); 6.46 (b s, 2H); 7.04 (m, 2H); 7.32 (m, 1H); 9.26 (s, 1H).

Mass spectrum (DCI—NH$_3$): 265 (M+H)$^+$, 282 (M+NH$_4$)$^+$, 189.

EXAMPLE 29

N-hydroxy-N-[1-(5-fluorobenzo[b]thien-2-yl)ethyl]urea a. 5-Fluorophenylbenzo[b]thiophene was prepared using the method of example 11, steps b, c, except using 4-fluorothiophenol instead of 4-t-butyl thiophenol.

b. N-benzyloxy-1-(5-fluorobenzo[b]thien-2-yl)ethyl amine. n-Butyl lithium (2.5M in hexanes, 4.4 mL) was added to a solution of 5-fluorobenzothiophene, prepared as described in part a, above (1.52 g, 10 mmole) in THF (25 mL) at −78° C. After stirring for 30 minutes borontrifluoride etherate was added followed by O-benzyl acetaldehyde oxime. Fifteen minutes later aqueous NH$_4$Cl was added and the reaction warmed to room temperature. The aqueous phase was extracted twice with ether and the combined organic layers washed twice with brine, dried over MgSO$_4$ and concentrated. The desired product was obtained as a yellow oil (2.9 g).

c. 1-(5-Fluorobenzo[b]thien-2-yl)ethyl hydroxylamine. The material prepared as in step a, above (1.48 g, 4.91 mmole) in methylene chloride (2 mL) was added to a solution of aluminum chloride in ethanethiol (15 mL) at 0° C. The ice bath was removed and the mixture was allowed to stir for 5 hours at room temperature. The mixture was poured onto ice and acidified with 10% aqueous HCl. The aqueous layer was extracted with ethyl acetate and the combined organic phases was dried over MgSO$_4$ and concentrated to give the desired product as a pale yellow powder (0.83 g).

d. N-hydroxy-N-[1-(5-fluorobenzo[b]thien-2-yl)ethyl]urea was prepared using the method of example 2, method a, except using the material prepared as in step c, above, instead of 1-(2-benzo[b]thienyl) ethyl hydroxyl amine. (R$_1$=NH$_2$, A=CHCH$_3$, X=S[2-isomer], Y=5-F).

Melting Point: 149°–153° C.

NMR (300 MHz, DMSO-d$_6$): 1.50 (d, 3H, J=7.5 Hz); 5.56 (m, 1H); 6.47 (br s, 2H); 7.13-7.29 (m, 2H); 7.57-7.77 (m, 1H); 7.81-7.95 (m, 1H); 9.26 (m, 1H).

Mass spectrum (DCI—NH$_3$): 255 (M+1)$^+$, 272 (M+NH$_4$)$^+$.

Analysis (C$_{11}$H$_{11}$FN$_2$O$_2$S): Calculated—C: 51.96, H: 4.36, N: 11.02; Found C: 52.05, H: 4.63, N: 10.46.

EXAMPLE 30

N-hydroxy-N-(2-benzo[b]thien-2-yl-1-methylethyl) urea a. 3-Benzo[b]thien-2-yl-2-nitroprop-2-ene. Sodium hydroxide (4M solution, 3.2 mL) was added to a solution of benzo[b]thiophene-2-carboxaldehyde (2.0 g, 12.3 mmole) and nitroethane (0.9 mL, 12.3 mmole) in methanol. The reaction was stirred at 5° C. for 1 hour and then allowed to warm to room temperature and stirred for 15 hours. The mixture was added to 3 ml of 6 N HCl and the desired product precipitated. It was collected by filtration and chromatographed on silica gel, eluting with 20% ether in hexanes.

b. 2-Benzo[b]thien-2-yl-1-methylethyl hydroxyl amine. A solution of the material prepared as in part a, above (0.56 g, 1.6 mmole) in THF (4 mL) was added to borane-THF complex at 0° C. The ice bath was removed and sodium borohydride (5 mg) was added. After being allowed to be stirred for 90 minutes ice water (~10 mL) was added followed by 10% HCl (3 mL). The solution was extracted with ether, then the aqueous layer was made basic by the addition of 2 N NaOH and extracted with ether. This ether phase was dried over MgSO$_4$ and evaporated to give the desired product (70 mg).

c. N-hydroxy-N-(2-benzo[b]thien-2-yl-1-methylethyl) urea. The desired material was prepared using the method of example 2, method a, except using the the material prepared as in step b, above, instead of 1-benzo[b]thien-2-ylethyl hydroxyl amine. (R$_1$=NH$_2$, A=CH$_2$CHCH$_3$, X=S[2-isomer], Y=H).

Melting Point: 141°–143° C.

NMR (300 MHz, DMSO-d$_6$): 1.05 (3H, d, d J=7.5 Hz); 2.88-3.11 (2H, m); 4.43 (1H, m); 6.33 (2H, br s); 7.18-7.36 (3H, m); 7.70-7.90 (2H, m); 9.07 (1H, br s).

Mass spectrum (DCI—NH$_3$): 251 (M+H)$^+$, 268 (M+NH$_4$)$^+$, 235, 208, 192.

Analysis (C$_{12}$H$_{14}$N$_2$O$_2$S): Calculated—C: 57.58, H: 5.64, N: 11.19; Found C: 57.68, H: 5.67, N: 11.14.

EXAMPLE 31

N-hydroxy-N-(3-benzo[b]thien-2-ylprop-2-enyl) acetamide a. 3-Benzo[b]thien-2-ylbromoprop-2-ene. Vinyl magnesium bromide (14.8 mmole) was added to a solution of 2-benzo[b]thiophene carboxaldehyde (2.0 g, 12.3 mmole) in THF (50 mL) at 0° C. After fifteen minutes the reaction mixture was cooled to −25° C. and HBr (48%, 12 mL) was added dropwise so that the temperature remained below 0° C. The mixture was allowed to warm to room temperature and allowed to stir for 1 hour. The solvent was then removed in vacuo. The residue was partitioned between water and ethyl acetate. The organic phase was evaporated to give a brown solid which was recrystallized from hexane/ethyl acetate. The desired product was obtained as a yellow solid (800 mg).

b. O-Tetrahydropyranyl-3-benzo[b]thien-2-ylprop-2-enyl hydroxylamine. Tetrahydropyranylhydroxyl amine (0.51 g, 4.34 mmole) in DMF (10 mL) was added to a solution of 3-benzo[b]thienylbromoprop-2-ene (0.50 g, 1.98 mmole) in DMF (10 mL). After being allowed to stir for two hours the reaction was poured into water and extracted with ether. The organic layer was washed with NaHCO$_3$ and brine. The organic layer was dried over MgSO$_4$ and evaporated. The residue was chromatographed on silica gel eluting with 40% ether in hexanes to give the desired product as a yellow oil (66%).

c. 3-Benzo[b]thien-2-ylprop-2-enyl hydroxylamine. A few drops of concentrated HCL was added to a solution of the material prepared as in part b, above (5.4 g) in methanol (150 mL) and stirred for three days. The solvent was removed to afford the desired product as its hydrochloride salt.

d. N-hydroxy-N-(3-benzo[b]thien-2-ylprop-2-enyl) acetamide was prepared using the method of example 1, steps d and e, except using the material prepared as in step c above, instead of 1-benzo[b]thien-2-ylethyl hydroxylamine. ($R_1$=$CH_3$, A=CH=CHCH$_2$, X=S[2-isomer], Y=H).

Melting Point: 168° C. dec.

NMR (300 MHz, DMSO-$d_6$): 204 (s, 3H); 4.30 (m, 2H); 6.06 (m, 1H); 6.88 (m, 1H); 7.35 (m, 3H); 7.83 (m, 2H); 10.05 (br s, 1H).

Mass spectrum (DCI−NH$_3$): 248 (M+H)$^+$, 265 (M+NH$_4$)$^+$, 232, 173.

Analysis ($C_{13}H_{13}NO_2S$): Calculated—C: 63.14, H: 5.30, N: 5.66; Found C: 61.13, H: 5.22, N: 5.43.

EXAMPLE 32

N-hydroxy-N-(3-benzo[b]thien-2-ylprop-2-enly)urea

The desired material was prepared according to the method of example 2, method a, except using 3-benzo[b]thienylprop-2-enyl hydroxylamine, prepared as in example 31, step c instead of 1-benzo[b]thien-2-ylethyl hydroxylamine. ($R_1$=NH$_2$, A=CH=CHCH$_2$, X=S[2-isomer], Y=H).

Melting Point: 167° C. dec.

NMR (300 MHz, DMSO-$d_6$): 4.13 (m, 2H); 6.10 (m, 1H); 6.43 (br s, 2H); 6.87 (m, 1H); 7.34 (m, 3H); 7.83 (m, 2H); 9.44 (s, 1H).

Mass spectrum (DCI−NH$_3$): 249 (M+1)$^+$, 266 (M+NH$_4$)$^+$, 233, 173.

Analysis ($C_{12}H_{12}N_2O_2S$): Calculated—C: 58.05, H: 4.87, N: 11.28; Found C: 57.74, H: 4.97, N: 11.00.

EXAMPLE 33

N-hydroxy-N-[1-(5-nitrobenzo[b]fur-2-yl)ethyl]urea

The desired material was prepared according to the method of example 22, except using 5-nitrosalicylaldehyde, instead of 5-chlorosalicylaldehyde. ($R_1$=NH$_2$, A=CHCH$_3$, X=O[2-isomer], Y=5-NO$_2$).

Melting Point: 175°–177° C. dec.

NMR (300 MHz, DMSO-$d_6$): 1.49 (d, 3, J=7.0 Hz); 5.52 (q, 1, J=7.0 Hz); 6.54 (br s, 2); 6.98 (s, 1); 7.78 (d, 1, J=8.8 Hz); 8.17 (dd, 1, J=8.8, 2.5 Hz); 8.57 (d, 1, J=2.5 Hz); 9.27 (s, 1).

Mass spectrum (CI−NH$_3$): 266 (M+1)$^+$, 283 (M+NH$_4$)$^+$.

Analysis ($C_{11}H_{11}N_3O_5$): Calculated—C: 49.81, H: 4.18, N: 15.84; Found C: 50.31, H: 4.39, N: 15.39.

EXAMPLE 34

N-hydroxy-N-[1-(5,7-dichlorobenzo[b]fur-2-yl)ethyl]urea

The desired material was prepared according to the method of example 22, except using 3,5-dichlorosalicylaldehyde, instead of 5-chlorosalicylaldehyde. ($R_1$=NH$_2$, A=CHCH$_3$, X=O[2-isomer], Y=5,7-Cl$_2$).

Melting Point: 140°–142° C.

NMR (300 MHz, DMSO-$d_6$): 1.46 (d, 3, J=6.8 Hz); 5.48 (q, 1, J=6.8 Hz); 6.56 (br s, 2); 6.85 (d, 1, J=0.7 Hz); 7.51 (d, 1, J=1.8 Hz); 7.69 (d, 1, J=1.8 Hz); 9.23 (s, 1).

Mass spectrum (CI−NH$_3$): 289 (M+1)$^+$, 306 (M+NH$_4$)$^+$.

Analysis ($C_{11}H_{10}Cl_2N_2O_3$): Calculated—C: 45.69, H: 3.49, N: 9.69; Found C: 45.78, H: 3.62, N: 9.57.

EXAMPLE 35

N-hydroxy-N-[1-(7-methoxybenzo[b]fur-2-yl)ethyl]urea

The desired material was prepared according to the method of example 22, except using 3-methoxysalicylaldehyde, instead of 5-chlorosalicylaldehyde. ($R_1$=NH$_2$, A=CHCH$_3$, X=O[2-isomer], Y=7-CH$_3$O).

Melting Point: 136°–137.5° C.

NMR (300 MHz, DMSO-$d_6$): 1.44 (d, 3, J-7.0 Hz); 3.90 (s, 3); 5.44 (q, 1, J=7.0 Hz); 6.46 (br s, 2); 6.69 (d, 1, J=1.1); 6.86 (m, 1); 7.11 (m, 2); 9.15 (s, 1).

Mass spectrum (CI−NH$_3$): 251 (M+1)$^+$, 268 (M+NH$_4$)$^+$, 175.

Analysis ($C_{12}H_{14}N_2O_4$): Calculated—C: 57.59, H: 5.64, N: 11.20; Found C: 57.71, H: 5.70, N: 11.21.

EXAMPLE 36

N-hydroxy-N-[1-(7-methoxybenzo[b]fur-2-yl)ethyl]N'-methyl urea

The desired material was prepared according to the method of example 22, except using 3-methoxysalicylaldehyde, instead of 5-chlorosalicylaldehyde and using methyl isocyanate instead of trimethylsilyl isocyanate ($R_1$=NHCH$_3$, A=CHCH$_3$, X=O[2-isomer], Y=7-CH$_3$O).

Melting Point: 135°–137° C.

NMR (300 MHz, DMSO-$d_6$): 1.44 (d, 3, J=7.0 Hz); 2.63 (d, 3, J=4.4 Hz); 3.91 (s, 3); 5.43 (q, 1, J=7.0 Hz); 6.69 (d, 1, J=1.1 Hz); 6.86 (dd, 1, J=2.7 Hz, J=6.1 Hz); 6.99 (br q, 1, J=4.4); 7.12 (m, 2); 9.09 (s, 1).

Mass spectrum (CI−NH$_3$): 265 (M+1)$^+$, 282 (M+NH$_4$)$^+$.

Analysis ($C_{13}H_{16}N_2O_4$): Calculated—C: 59.08, H: 6.10, N: 10.60; Found C: 59.16, H: 6.09, N: 10.60.

EXAMPLE 37

N-hydroxy-N-[1-(7-methoxybenzo[b]fur-2-yl)ethyl]urea

The desired material was prepared according to the method of example 22, except using 3-ethoxysalicylaldehyde, instead of 5-chlorosalicylaldehyde. ($R_1$=NH$_2$, A=CHCH$_3$, X=O[2-isomer], Y=7-CH$_3$CH$_2$O).

Melting Point: 146°–148° C.

NMR (300 MHz, DMSO-$d_6$): 1.40 (t, 3, J=7.0); 1.44 (d, 3, J=7.0); 4.20 (q, 2, J=7.0); 5.45 (q, 1, J=7.0); 6.49 (br s, 2); 6.70 (d, 1, J=0.7); 6.85 (dd, 1, J=2.2, J=6.6); 7.11 (m, 2); 9.14 (s, 1).

Mass spectrum (CI−NH$_3$): 265 (M+1)$^+$, 282 (M+NH$_4$)$^+$, 189.

Analysis ($C_{13}H_{16}N_2O_4$): Calculated—C: 59.08, H: 6.10, N: 10.60; Found C: 59.06, H: 6.17, N: 10.50.

EXAMPLE 38

N-hydroxy-N-(1-indol-2-ylethyl)N'-methyl urea a. 2-Acetylindole. n-Butyl lithium (40 mL, 2.5 M in hexanes, 100 mmole) was added dropwise to a solution of indole (11.7 g, 100 mmole) in dry THF (100 mL) at −70° C. After thirty minutes the mixture was added via cannula to an excess of carbon dioxide (dry ice, 18 g) in THF (100 mL). The solution was then allowed to warm to room temperature. The solvent was evaporated in vacuo to give indole-1-carboxylic acid, lithium salt, as a white solid. Benzene (50 mL) was added to the mixture and distilled away to remove traces of water. Fresh THF (100 mL) was added to the solid and the solution was cooled to −70° C. t-Butyl lithium (63 mL, 1.6 M in pentane, 100 mmole) was slowly added to the solution. The mixture was allowed to stir at −70° C. for 1 hour and then N,O-dimethyl acetohydroxamic acid (10.3 g, 100 mmole) was added in THF (100 mL). The solution was stirred for an additional 2 hours at −70° C. and then at 0° C. for 1 hour. The reaction was quenched by the addition of ammonium chloride (20 mL, saturated). The mixture was extracted with ethyl acetate, and the organic phase dried over sodium sulfate and the solvent removed in vacuo. The residue was chromatographed on silica gel, eluting with methylene chloride to afford the desired material as a white solid (10.4 g, 66%).

b. N-hydroxy-N-(1-indol-2-ylethyl)N'-methyl urea. The desired product was obtained using the method of example 2, method a, except using the material prepared as in step a, above instead of 2-acetylbenzothiophene and using methyl isocyanate instead of trimethylsilyl isocyanate. ($R_1$=NHCH$_3$, A=CHCH$_3$, X=NH[2-isomer], Y=H).

Melting Point: 164°–165° C.

NMR (300 MHz, DMSO-$d_6$): 1.48 (d, 2H, J=7 Hz); 3.60 (br s, 3H); 5.51 (q, 1H, J=7 Hz); 6.31 (br s, 1H); 6.95 (m, 1H); 7.05 (m, 1H); 7.32 (m, 1H); 7.45 (m, 1H); 9.21 (s, 1H); 10.82 (br s, 1H).

IR (KBr): 3310, 2980, 2920, 1660, 1580, 1480, 1460, 1420, 1375, 1320, 1220, 1240, 1140, 1120, 1000, 900, 860, 800, 760, 740, 680, 600, 495.

Mass spectrum (DCI−NH$_3$): 234 (M+H)$^+$, 247 (M+NH$_4$)$^+$, 144.

EXAMPLE 39

N-hydroxy-N-[1-(5-chloroindol-2-yl)ethyl]N'-methyl urea

The desired material was prepared according to the method of example 38, except using 5-chloroindole, instead of indole and using trimethylsilyl isocyanate instead of methylisocyanate ($R_1$=NH$_2$, A=CHCH$_3$, X=NH[2-isomer], Y=5-Cl).

Melting Point: 159°–160° C.

NMR (300 MHz, DMSO-$d_6$): 1.55 (d, J=7 Hz, 3H); 5.52 (q, J=7 Hz, 1H); 6.35 (s, 1H); 6.51 (br s, 2H); 7.10 (m, 1H); 7.43 (m, 1H); 7.58 (m, 1H); 9.21 (s, 1H); 11.15 (s, 1H).

IR (KBr): 3460, 3420, 3350, 3280, 3200, 3000, 1660, 1580, 1460, 1440, 1420, 1320, 1160, 1120, 1060, 1000, 900, 880, 860, 800, 760, 720, 690, 660, 600, 470.

Mass spectrum (DCI−NH$_3$): 254 (M+H)$^+$, 271 (M+NH$_4$)$^+$, 178.

EXAMPLE 40

N-hydroxy-N-[1(1-acetylindol-2-yl)ethyl]urea a. N-hydroxy-N-(1-indol-2-yl)ethyl urea was prepared according to the method of example 38, except using trimethylsilyl isocyanate instead of methylisocyanate. (See also example 54.)

b. N-acetoxy-N-[1-(1-acetylindol-2-yl)ethyl]urea. Lithium cyanide (4 mL of a 0.5 M solution in DMF) was added to a solution of the material prepared as in step a, above (0.22 g, 1 mmole) in THF (20 mL). Acetyl chloride (0.14 mL, 2 mmole) in THF (5 mL) was then added dropwise. After 3 hours the solvent was removed in vacuo and the residue partitioned between water (30 mL) and ethyl acetate (60 mL). The organic layer was separated and washed with brine and dried over sodium sulfate. The solvent was evaporated and the residue recrystallized from ether/ethyl acetate to give the desire product as a colorless solid (58%, 175 mg).

c. N-hydroxy-N-[1-(1-acetylindol-2-yl)ethyl]urea. The material prepared as in step b, above (175 mg) was dissolved in isopropanol/water (2/1, 20 mL) and lithium hydroxide (50 mg, 1.2 mmole) was added in water (1 mL). The mixture was allowed to stir for 30 min, saturated ammonium chloride was added (50 mL) and the desired product extracted into ethyl acetate. The organic phase was washed with brine and dried over sodium sulfate. The solvent was removed in vacuo and the residue recrystallized from ether/ethyl acetate to afford the desired product as a white solid (135 mg, 73%). ($R_1$=NH$_2$, A=CHCH$_3$, X=NCOCH$_3$[2-isomer], Y=H).

Melting Point: 146°–147° C.

NMR (300 MHz, DMSO-$d_6$): 1.52 (d, 3H, J=7 Hz); 2.21 (s, 3H); 5.45 (q, 1H, J=7 Hz); 6.32 (s, 1H); 6.55 (br s, 2H); 6.95 (m, 1H); 7.05 (m, 1H); 7.35 (m, 1H); 7.45 (m, 1H); 10.52 (s, 1H).

IR (KBr): 3300, 3150, 3000, 2900, 1660, 1650, 1500, 1380, 1220, 1150, 1100, 1000, 950, 780, 750.

Mass spectrum (DCI−NH$_3$): 262 (M+H)$^+$, 279 (M+NH$_4$)$^+$, 219.

EXAMPLE 41

N-hydroxy-N-[1-(1-methanesulfonylindol-2-yl)ethyl]urea

The desired material was prepared as described in example 38, except using 1-methanesulfonyl indole instead of indole and using trimethylsilyl isocyanate instead of methyl isocyanate. ($R_1$=NH$_2$, A=CHCH$_3$, X=NSO$_2$CH$_3$[2-isomer], Y=H).

Melting Point: 166°–167° C.

NMR (300 MHz, DMSO-$d_6$): 1.50 (d, 3H, J=7 Hz); 3.55 (s, 3H); 5.42 (q, 1H, J=7 Hz); 6.35 (s, 1H); 6.50 (br s, 2H); 6.95 (m, 1H); 7.08 (m, 1H); 7.32 (m, 1H); 7.43 (m, 1H); 10.47 (s, 1H).

IR (KBr): 3300, 3150, 2900, 1650, 1340, 1160, 1495, 1215, 1100.

Mass spectrum (DCI−NH$_3$): 298 (M+H)$^+$, 315 (M+NH$_4$)$^+$.

EXAMPLE 42

N-hydroxy-N-benzo[b]thien-7-ylmethyl urea a. 7-Methylbenzo[b]thiophene was prepared using the method of example 11, steps b, c, except using 2-methylthiophenol instead of 4-t-butyl thiophenol.

b. 7-Bromomethylbenzo[b]thiophene. N-bromosuccinimide (4.32 g, 24.3 mmole) and the material prepared as in step a, above (3.61 g, 24.3 mmole) were suspended in CCl$_4$ (50 mL). Benzoyl peroxide (0.59 g, 2.43 mmole) was added and the suspension was heated at reflux for 3 hours. The reaction mixture was cooled to room temperature and solid filtered off. The filtrate was dried over MgSO$_4$ and concentrated in vacuo. The residue was chromatographed on silica gel eluting with hexane followed by ether to afford the desired product.

c. 7-Hydroxymethylbenzo[b]thiophene. The material prepared as in step b, above (1.3 g, 5.7 mmole) was dissolved in dioxane (15 mL) and 2N NaOH was added. The mixture was allowed to stir three days at room temperature. The mixture was extracted twice with ether and the combined organic layers were washed with brine, dried over MgSO$_4$ and concentrated. The residue was chromatographed on silica gel eluting with 50% ether in hexanes to afford the desired product as a yellow powder (0.49 g).

d. Benzo[b]thiophene-7-carboxaldehyde. A solution of the material prepared as in step c, above (0.49 g) in benzene was added to a suspension of manganese dioxide on carbon (5.0 g) and heated at reflux for 3 hours. The reaction mixture was filtered and concentrated to afford the desired product as a yellow oil (0.4 g).

e. N-hydroxy-N-benzo[b]thien-7-ylmethyl urea was prepared using the method of example 2, method a, except using the material prepared as in step d, above, instead of 2-acetylbenzo[b]thiophene. (R$_1$=NH$_2$, A=CH$_2$, X=S[7-isomer], Y=H).

Melting Point: 138°–140.5° C.

NMR (300 MHz, DMSO-d$_6$): 4.77 (s, 2H); 6.46 (br s, 2H); 7.30 (m, 1H); 7.37 (m, 1H); 7.49 (d, 1H, J=6 Hz); 7.75 (d, 1H, 6 Hz); 7.81 (m, 1H); 9.39 (s, 1H).

Mass spectrum (DCI−NH$_3$): 223 (M+H)$^+$, 240 (M+NH$_4$)$^+$.

Analysis (C$_{10}$H$_{10}$N$_2$O$_2$S): Calculated—C: 54.04, H: 4.54, N: 12.60; Found C: 53.87, H: 4.67, N: 12.44.

EXAMPLE 43

N-hydroxy-N-[1-(2,3-dihydrobenzo[b]fur-yl)ethyl]urea a. 1-(2,3-dihydrobenzo[b]fur-2-yl)ethanol. A suspension of palladium on carbon (10%, 220 mg) and 2-acetyl benzo[b]furan (19.5 g, 122 mmole) was allowed to stir for 48 hours under an atmosphere of hydrogen (pressure=1 atm). The mixture was filtered through celite and the filtrate was concentrated. The residue was chromatographed on silica gel (300 g) eluting with 25% ethyl acetate in hexanes to afford the desired product.

b. 2-Acetyl-2,3-dihydrobenzo[b]furan. A solution of dry DMSO (18.0 g, 230 mmole) in methylene chloride (30 mL) was added to a solution of oxalyl chloride (14.5 g, 114.2 mmole) in methylene chloride (100 mL) at −60° C. Thirty minutes later the alcohol prepared as in step a, above (15.1 g, 92 mmole) in methylene chloride (75 mL) was added. The resulting suspension was stirred at −60° C. for 1 hour and then triethylamine (48 g, 474 mmole) was added. The mixture was allowed to stir at room temperature for 15 hours. The mixture was washed with water, 5% HCl, saturated NaCl, and dried over MgSO$_4$. The solvent was removed in vacuo to yield the desired product as a light yellow oil.

c. N-hydroxy-N-[1-(2,3-dihydrobenzo[b]fur-2-yl)ethyl]urea. The desired material was prepared using the method of example 2, method a, except using the material prepared as described in step b, instead of 2-acetylbenzo[b]thiophene. (R$_1$=NH$_2$, A=CHCH$_3$, X=O[2-isomer], Y=2,3-dihydro)

Melting Point: 129°–131° C.

NMR (300 MHz, DMSO-d$_6$): Mixture of diasteriomers 1.04, 1.17 (d, 3 J=6.8); 2.98 (m, 1); 3.22 (m, 1); 4.07, 4.34 (m, 1); 4.66, 4.75 (m, 1); 6.29, 6.41 (br s, 2 ); 6.67–6.80 (m, 2); 7.07, 7.19 (m, 1); 9.12, 9.15 (s, 1).

Mass spectrum (DCI−NH$_3$): 223 (M+H)$^+$, 240 (M+NH$_4$)$^+$.

Analysis (C$_{11}$H$_{14}$N$_2$O$_3$): Calculated—C: 59.44, H: 6.35, N: 12.61; Found C: 59.41, H: 6.37, N: 12.60.

EXAMPLE 44

N,N'-dihydroxy-N-(1-benzo[b]thien-2-ylethyl) urea

The desired material was prepared according to the method of example 2, method b, except using hydroxylamine instead of ammonium hydroxide. (R$_1$=NHOH, A=CHCH$_3$, X=S[2-isomer], Y=H).

Melting Point: 132°–134° C. dec.

NMR (300 MHz, DMSO-d$_6$): 1.52 (3H, d, J=7.5 Hz); 5.49 (1H, q, J=7.5 Hz); 7.26–7.37 (3H, m); 7.74–7.92 (2H, m); 8.42 (1H, br s); 9.15 (1H, br s); 9.00 (1H, br s).

Mass spectrum (DCI−NH$_3$): 253 (M+H)$^+$, 270 (M+NH$_4$)$^+$, 237, 221, 176, 161.

EXAMPLE 45

N-hydroxy-N-(1-benzo[b]thien-2-ylethyl)N'-ethylurea

The desired material was prepared according to the method of example 2, method a, except using ethyl isocyanate instead of trimethylsilyl isocyanate. (R$_1$=NHCH$_2$CH$_3$, A=CHCH$_3$, X=S[2-isomer], Y=H).

Melting Point: 138°–139° C.

NMR (300 MHz, DMSO-d$_6$): 1.01 (t, 3H, J=7.5 Hz); 1.52 (d, 3H, J=7.5 Hz); 3.00–3.18 (m, 2H); 5.56 (q, 1H, J=7.5); 7.05 (m, 1H); 7.22–7.40 (m, 3H); 7.70–7.95 (m, 2H); 9.18 (g, 1H).

Mass spectrum (DCI−NH$_3$): 265 (M+H)$^+$, 282 (M+NH$_4$)$^+$, 176, 161, 157.

Analysis (C$_{13}$H$_{16}$N$_2$O$_2$S): Calculated—C: 59.07, H: 6.10, N: 10.60; Found C: 58.92, H: 6.24, N: 10.58.

EXAMPLE 46

N-hydroxy-N-(1-benzo[b]thien-2-ylethyl)N'-methyl thiourea

The desired material was prepared according to the method of example 2, method a, except using methyl isothiocyanate instead of trimethylsilyl isocyanate. (R$_1$=NHCH$_3$, A=CHCH$_3$, X=S[2-isomer], Y=H; Z=S).

Melting Point: 154°–155° C.

NMR (300 MHz, DMSO-d$_6$): 1.59 (d, 3H, J=7.5 Hz); 2.91 (d, 3H, J=4.5 Hz); 6.74 (qt, 1H, J=7.5 Hz); 7.25–7.40 (m, 3H); 7.75–7.93 (m, 2H); 8.38 (q, 1H, J=4.5 Hz); 9.68 (s, 1H).

Mass spectrum (DCI−NH$_3$): 267 (M+H)$^+$, 284 (M+NH$_4$)$^+$, 194, 176, 161.

Analysis (C$_{12}$H$_{14}$N$_2$OS$_2$): Calculated—C: 54.11, H: 5.30, N: 10.52; Found C: 53.98, H: 5.31, N: 10.49.

EXAMPLE 47

N-hydroxy-N-benzo[b]thien-2-ylmethylN'-methyl urea

The desired material was prepared according to the method of example 2, method a, except using 2-benzo[b]thiophene carboxaldehyde instead of 2-acetylbenzo[b]thiophene and using methyl isocyanate instead of trimethylsilyl isocyanate. ($R_1$=NHCH$_3$, A=CH$_2$, X=S[2-isomer], Y=H).

Melting Point: 160°–161° C.

NMR (300 MHz, DMSO-d$_6$): 2.61 (d, 3H, J=4.5 Hz); 4.74 (s, 2H); 7.01 (q, 1H, J=4.5 Hz); 7.26–7.38 (m, 3H); 7.74–7.97 (m, 2H); 9.46 (s, 1H)

Mass spectrum (CI−NH$_3$): 237 (M+1)$^+$, 254 (M+NH$_4$)$^+$.

EXAMPLE 48

N-hydroxy-N-benzo[b]thien-2-ylmethyl-N'-ethyl urea

The desired material was prepared according to the method of example 2, method a, except using ethyl isocyanate instead of trimethylsilyl isocyanate and using 2-benzo[b]thiophene carboxaldehyde instead of 2-acetylbenzothiophene. ($R_1$=NHCH$_2$CH$_3$, A=CH$_2$, X=S[2-isomer], Y=H).

Melting Point: 128°–129° C.

NMR (300 MHz, DMSO-d$_6$): 1.01 (t, 3H$^3$, J=7.5 Hz); 3.03–3.15 (m, 2H$^2$); 4.74 (s, 2H), 7.02–7.10 (t, 1H, J=6.0 Hz); 7.26–7.38 (m, 3H); 7.75–7.80 (m, 1H); 7.87–7.93 (m, 1H); 9.46 (s, 1H).

Mass spectrum (DCI−NH$_3$): 251 (M+H)$^+$, 268 (M+NH$_4$)$^+$, 180, 162, 147, 134.

Analysis (C$_{12}$H$_{14}$N$_2$O$_2$S): Calculated—C: 57.58, H: 5.64, N: 11.19; Found C: 57.65, H: 5.73, N: 10.96.

EXAMPLE 49

N-hydroxy-N-(1-benzo[b]thien-2-yl)-3-methylpropyl urea

The desired material was prepared according to the method of example 2, method a, except using 2-isobutyrylbenzo[b]thiophene instead of 2-acetylbenzo[b]thiophene. ($R_1$=NH$_2$, A=CH(CH$_2$CH(CH$_3$)$_2$), X=S[2-isomer], Y=H).

NMR (300 MHz, DMSO-d$_6$): 0.92 (m, 3H); 1.67 (m, 2H), 1.91 (m, 1H), 5.51 (m, 1H); 6.39 (s, 2H); 7.27 (s, 1H); 7.31 (m, 1H); 7.78 (m, 1H); 7.87 (m, 1H); 9.24 (s, 1H).

Mass spectrum (DCI−NH$_3$): 296 (M+H)$^+$, 279 (M+NH$_4$)$^+$, 261, 203, 147.

EXAMPLE 50

N-hydroxy-N-benzo[b]fur-2-ylmethyl urea

The desired material was prepared according to the method of example 2, method a, except using 2-benzo[b]furan carboxaldehyde instead of 2-acetylbenzothiophene. ($R_1$=NH$_2$, A=CH$_2$, X=O[2-isomer], Y=H).

Melting Point: 161°–162° C.

NMR (300 MHz, DMSO-d$_6$): 4.66 (s, 2H); 6.51 (s, 2H); 6.77 (s, 1H); 7.18–7.30 (m, 2H); 7.50–7.63 (m, 2H); 9.54 (s, 1H).

IR (KBr): 1575, 1630, 1670, 3490.

Mass spectrum (DCI−NH$_3$): 207 (M+H)$^+$, 224 (M+NH$_4$)$^+$, 191, 162, 146, 131.

Analysis (C$_{10}$H$_{10}$N$_2$O$_3$): Calculated—C: 58.25, H: 4.89, N: 13.59; Found C: 57.86, H: 5.01, N: 13.52.

EXAMPLE 51

N-hydroxy-N-benzo[b]fur-2-ylmethylN'-methyl urea

The desired material was prepared according to the method of example 2, method a, except using 2-benzo[b]furan carboxaldehyde instead of 2-acetylbenzothiophene and using methyl isocyanate instead of trimethylsilyl isocyanate. ($R_1$=NHCH$_3$, A=CH$_2$, X=O[2-isomer], Y=H).

Melting Point: 126°–128° C.

NMR (300 MHz, DMSO-d$_6$): 2.63 (d, 3H, 4.5 Hz); 4.65 (s, 2H); 6.75 (s, 1H); 7.05 (q, 1H, 4.5 Hz); 7.18–7.30 (m, 2H); 7.50–7.61 (m, 2H); 9.48 (s, 1H).

IR (KBr): 1538, 1660, 3450, 3530.

Mass spectrum (DCI−NH$_3$): 221 (M+H)$^+$, 238 (M+NH$_4$)$^+$, 203, 146, 131.

analysis (C$_{11}$H$_{12}$N$_2$O$_3$): Calculated—C: 59.99, H: 5.49, N: 12.72; Found C: 59.76, H: 5.34, N: 12.66.

EXAMPLE 52

N-hydroxy-N-[1-(6-phenylmethoxybenzo[b]fur-2-yl)ethyl]urea

The desired material was prepared according to the method of example 22, except using 4-benzyloxysalicylaldehyde instead of 5-chlorosalicylaldehyde. ($R_1$=NH$_2$, A=CH$_2$, X=O[2-isomer], Y=C$_6$H$_5$CH$_2$O).

Melting Point: 153°–155° C.

NMR (300 MHz, DMSO-d$_6$): 1.42 (d, 3, J=6.6); 5.13 (s, 2); 5.42 (q, 1, J=6.6); 6.43 (br s, 2); 6.61 (s, 1); 6.91 (dd, 1, J=2.2, J=8.5); 7.19 (d, 1, J=2.22); 7.27–7.50 (m, 6); 9.13 (s, 1).

Mass spectrum (DCI−NH$_3$): 327 (M+H)$^+$, 344 (M+NH$_4$)$^+$, 251.

Analysis (C$_{18}$H$_{18}$N$_2$O$_4$): Calculated—C: 66.24, H: 5.56, N: 8.59; Found C: 65.71, H: 5.46, N: 8.19.

EXAMPLE 53

N-hydroxy-N-[1-(6-phenylmethoxybenzo[b]fur-2-yl)ethyl]N'-methyl urea

The desired material was prepared according to the method of example 22, except using 4-benzyloxysalicylaldehyde instead of 5-chlorosalicylaldehyde and using methyl isocyanate instead of trimethylsilyl isocyanate. ($R_1$=NHCH$_3$, A=CH$_2$, X=O[2-isomer], Y=C$_6$H$_5$CH$_2$O).

Melting Point: 172.5°–174° C.

NMR (300 MHz, DMSO-d$_6$): 1.43 (d, 3, J=7.0); 2.63 (d, 3, J=7.0); 5.14 (s, 2); 5.40 (br q, 1, J=7.0); 6.62 (m, 1); 6.91 (dd, 1, J=2.2, J=8.5); 6.97 (br q, 1, J-7.0); 7.20 (d, 1, J=2.2); 7.30–7.50 (m, 6); 9.06 (s, 1).

Mass spectrum (DCI−NH$_3$): 341 (M+H)$^+$, 358 (M+NH$_4$)$^+$, 251.

Analysis (C$_{19}$H$_{20}$N$_2$O$_4$): Calculated—C: 67.04, H: 5.92, N: 8.23; Found C: 66.87, H: 5.86, N: 8.14.

EXAMPLE 54

N-hydroxy-N-(1-indol--2-yl)ethyl)urea

The desired material was prepared according to the method of example 38, except using trimethylsilyl isocyanate instead of methylisocyanate. ($R_1$=NH$_2$, A=CHCH$_3$, X=NH[2-isomer], Y=H).

Melting Point: 159°–160° C.

NMR (300 MHz, DMSO-d$_6$): 1.48 (d, 3H, J=7 Hz); 5.46 (q, 1H, J=7 Hz); 6.28 (s, 1H); 6.45 (br s, 2H); 6.93 (m, 1H); 7.03 (m, 1H); 7.33 (m, 1H); 7.43 (m, 1H); 8.05 (s, 1H); 10.75 (br s, 1H).

Mass spectrum (DCI−NH$_3$): 220 (M+H)$^+$, 237 (M+NH$_4$)$^+$, 144.

Examples 55–60 are prepared in a manner generally analogous to methods of example 2.

EXAMPLE 55

N-hydroxy-N-[1-(3-hydroxybenzo[b]thien-2-yl)ethyl]urea ($R_1$=NH$_2$, A=CHCH$_3$, X=S[2-isomer], Y=3-OH).

EXAMPLE 56

N-hydroxy-N-[1-(5-trifluoromethylbenzo[b]thien-2-yl)ethyl]urea ($R_1$=NH$_2$, A=CHCH$_3$, X=S[2-isomer], Y=5-CF$_3$).

EXAMPLE 57

N-hydroxy-N-[1-(7-methoxybenzo[b]thien-2-yl)ethyl]urea ($R_1$=NH$_2$, A=CHCH$_3$, X=S[2-isomer], Y=7-OCH$_3$).

EXAMPLE 58

N-hydroxy-N-[1-(5-phenylbenzo[b]thien-2-yl)ethyl]urea ($R_1$=NH$_2$, A=CHCH$_3$, X=S[2-isomer], Y=5-C$_6$H$_5$).

EXAMPLE 59

N-hydroxy-N-[1-(5-phenylmethoxy-benzo[b]thien-2-yl)ethyl]urea ($R_1$=NH$_2$, A=CHCH$_3$, X=S[2-isomer], Y=5-C$_6$H$_5$CH$_2$O).

EXAMPLE 60

N-hydroxy-N-[1-(2-benzo[b]thien-2-yl)propyl]urea ($R_1$=NH$_2$, A=CHCH$_2$CH$_3$, X=S[2-isomer], Y=H).

Examples 61–67 are prepared in a manner generally analogous to methods of example 1.

EXAMPLE 61

N-hydroxy-N-(1-benzo[b]thien-2-ylethyl) propionamide ($R_1$=CH$_3$CH$_2$, A=CHCH$_3$, X=S[2-isomer], Y=H).

EXAMPLE 62

N-hydroxy-N-(1-benzo[b]thien-2-ylethyl)propenamide ($R_1$=CH$_2$=CH, A=CHCH$_3$, X=S[2-isomer], Y=H).

EXAMPLE 63

N-hydroxy-N-indol-2-ylmethyl acetamide ($R_1$=CH$_3$, A=CH$_2$, X=NH[2-isomer], Y=H).

EXAMPLE 64

N-hydroxy-N-(1-benzo[b]thien-3-ylethyl)acetamide ($R_1$=CH$_3$, A=CHCH$_3$, X=S[3-isomer], Y=H).

EXAMPLE 65

N-hydroxy-N-[1-(5-fluorobenzo[b]fur-2-yl)ethyl]acetamide ($R_1$=CH$_3$, A=CHCH$_3$, X=O[2-isomer], Y=5-F).

EXAMPLE 66

N-hydroxy-N-(1(5-phenoxybenzo[b]fur-2-yl)ethyl)acetamide ($R_1$=CH$_3$, A=CHCH$_3$, X=O[2-isomer], Y=5-C$_6$H$_5$O).

EXAMPLE 67

N-hydroxy-N-[1-(5-(4-fluorophenyl)methyl)benzo[b]thien-2-yl)ethyl]acetamide ($R_1$=CH$_3$, A=CHCH$_3$, X=O[2-isomer], Y=5-(4-FC$_6$H$_5$)CH$_2$).

EXAMPLE 68

N-hydroxy-N-(1-benzo[b]thien-2-ylethyl)urea potassium salt

The desired material is prepared as described in example 19 except potassium bis(trimethylsilyl) amide is used instead of sodium bis(trimethylsilyl) amide.

($R_1$=NH$_2$, A=CHCH$_3$, X=S[2-isomer], Y=H, M=K).

EXAMPLE 69

N-hydroxy-N-(1-benzo[b]thien-2-ylethyl)acetamide ammonium salt

The desired material is prepared as described in example 19 except ammonia is used instead of sodium bis(trimethylsilyl) amide. ($R_1$=CH$_3$, A=CHCH$_3$, X=S[2-isomer], Y=H, M=NH$_4$).

EXAMPLE 70

N-hydroxy-N-(1-benzo[b]thien-2-ylethyl)acetamide triethyl ammonium salt

The material prepared as in example 1 is dissolved in tetrahydrofuran and one equivalent of triethylamine is added. The solvent is removed in vacuo to yield the desired product. $R_1$=CH$_3$, A=CHCH$_3$, X=S[2-isomer], Y=H, M=NH(C$_2$H$_5$)$_3$.

EXAMPLE 71

N-hydroxy-N-(1-benzo[b]thien-2-ylethyl)acetamide tetraethyl ammonium salt

The material prepared as in example 1 is dissolved in tetrahydrofuran and one equivalent of tetraethylammonium hydroxide is added. The solvent is removed in vacuo to yield the desired product. $R_1$=CH$_3$, A=CHCH$_3$, X=S [2-isomer], Y=H, M=N(C$_2$H$_5$)$_4$.

EXAMPLE 72

N-butyryloxy-N-(1-benzo[b]thien-2-ylethyl)urea

The material prepared as in example 2 and 1.1 equivalent of triethylamine are dissolved in tetrahydrofuran and 1 equivalent of butyryl chloride is added. Ether is added and the material is washed with 2N HCl, dried with MgSO$_4$ and then evaporated in vacuo to yield the desired product. ($R_1$=NH$_2$, A=CHCH$_3$, X=S[2-isomer], Y=H, M=COC$_3$H$_7$).

EXAMPLE 73

N-benzoyloxy-N-(1-benzo[b]thienylethyl)urea

The material prepared as in example 2 and 1.1 equivalent of triethylamine are dissolved in tetrahydrofuran and 1 equivalent of benzoyl chloride is added. Ether is added and the material is washed with 2N HCl, dried with MgSO$_4$ and then evaporated in vacuo to yield the desired product. (R$_1$=NH$_2$, A=CHCH$_3$, X=S[2-isomer], Y=H, M=COC$_6$H$_5$).

EXAMPLE 74

Lipoxygenase IC$_{50}$ Determination

Assays to determine 5-lipoxygenase inhibitory activity were performed in 200 μL incubations containing the 20,000×g supernatant from 6×10$^4$ homogenized RBL-1 cells, 2% DMSO vehicle and various concentrations of the test compound. Reactions were initiated by addition of radiolabelled arachidonic acid and terminated by acidification and ether extraction. Reaction products were separated from nonconverted substrate by thin layer chromatography and measured by liquid scintillation spectroscopy. All treatments were evaluated in triplicate incubations. Inhibition of 5-lipoxygenase activity was computed by comparison of the quantity of products formed in the treatment incubations to the mean product formation in vehicle control groups (n=8). IC$_{50}$ values and 95% confidence limits were computed by linear regression analysis of percentage inhibition versus log inhibitor concentration plots. Inhibitory potencies for representative examples of compounds of this invention are listed in Table 1.

TABLE 1

In vitro 5-lipoxygenase inhibitory potency of compounds of this invention

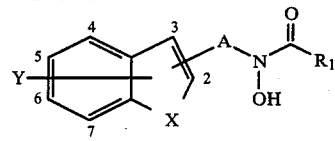

| Ex | R$_1$ | A | X | Y | Attached* | IC$_{50}$(μM) |
|---|---|---|---|---|---|---|
| 1 | CH$_3$ | CHCH$_3$ | S | H | 2 | 1.1 |
| 2 | NH$_2$ | CHCH$_3$ | S | H | 2 | 0.65 |
| 3 | NHCH$_3$ | CHCH$_3$ | S | H | 2 | 0.65 |
| 4 | N(CH$_3$)$_2$ | CHCH$_3$ | S | H | 2 | 0.54 |
| 5 | CH$_3$ | CH$_2$ | S | H | 2 | 1.6 |
| 6 | NH$_2$ | CH$_2$ | S | H | 2 | 1.9 |
| 7 | N(CH$_3$)$_2$ | CH$_2$ | S | H | 2 | 1.1 |
| 8 | CH$_3$ | CHCH$_3$ | S | H | 3 | 1.4 |
| 9 | NH$_2$ | CHCH$_3$ | S | H | 3 | 1.3 |
| 10 | NH$_2$ | CHCH$_3$ | S | 3-CH$_3$ | 2 | 0.54 |
| 11 | NH$_2$ | CHCH$_3$ | S | 5-(CH$_3$)$_3$C | 2 | 0.71 |
| 12 | CH$_3$ | CHCH$_3$ | SO$_2$ | H | 2 | 21 |
| 14 | CH$_3$ | CHCH$_3$ | O | H | 2 | 1.9 |
| 15 | NH$_2$ | CHCH$_3$ | O | H | 2 | 2.7 |
| 16 | CH$_3$ | CHCH$_3$ | NCH$_3$ | H | 3 | 2.6 |
| 17 | NH$_2$ | CHCH$_3$ | NCH$_3$ | H | 3 | 2.8 |
| 18 | NHCH$_3$ | CHCH$_3$ | NCH$_3$ | H | 3 | 3.7 |
| 20 | H | CHCH$_3$ | S | H | 2 | 3.0 |
| 21 | (CH$_3$)$_2$CH | CHCH$_3$ | S | H | 2 | 0.38 |
| 22 | NH$_2$ | CHCH$_3$ | O | 5-CH$_3$O | 2 | 1.7 |
| 23 | NH$_2$ | CHCH$_3$ | O | 5-Cl | 2 | 0.81 |
| 24 | NH$_2$ | CHCH$_3$ | NCH$_3$ | H | 2 | 1.6 |
| 25 | NH$_2$ | CHCH$_3$ | S | H | 2 | Z=S | 0.19 |
| 26 | NH$_2$ | CHCH$_3$ | S | 3-CH$_3$O | 2 | 0.66 |
| 28 | NH$_2$ | CHCH$_3$ | S | 4,7-(CH$_3$)$_2$ | 2 | 0.40 |
| 29 | NH$_2$ | CHCH$_3$ | S | 5-F | 2 | 0.50 |
| 30 | NH$_2$ | CH$_2$CHCH$_3$ | S | H | 2 | 0.46 |
| 31 | CH$_3$ | CH=CHCH$_2$ | S | H | 2 | 0.27 |
| 32 | NH$_2$ | CH=CHCH$_2$ | S | H | 2 | 0.35 |
| 33 | NH$_2$ | CHCH$_3$ | O | 5-NO$_2$ | 2 | 2.0 |
| 34 | NH$_2$ | CHCH$_3$ | O | 5,7-Cl$_2$ | 2 | 0.36 |
| 35 | NH$_2$ | CHCH$_3$ | O | 7-CH$_3$O | 2 | 1.9 |
| 37 | NH$_2$ | CHCH$_3$ | O | 7-CH$_3$CH$_2$O | 2 | 3.5 |
| 38 | NH$_2$ | CHCH$_3$ | NH | H | 2 | 2.9 |
| 39 | NH$_2$ | CHCH$_3$ | NH | 5-Cl | 2 | 1.0 |
| 40 | NH$_2$ | CHCH$_3$ | NCOCH$_3$ | H | 2 | 4.0 |
| 41 | NH$_2$ | CHCH$_3$ | NSO$_2$CH$_3$ | H | 2 | 3.0 |
| 42 | NHCH$_3$ | CH$_2$ | S | H | 7 | 7.2 |
| 43 | NH$_2$ | CHCH$_3$ | O | 2,3-dihydro | 2 | 8.5 |
| 44 | NHOH | CHCH$_3$ | S | H | 2 | 0.51 |
| 45 | NHCH$_2$CH$_3$ | CHCH$_3$ | S | H | 2 | 1.8 |
| 46 | NHCH$_3$ | CHCH$_3$ | S | H | 2 | Z=S | 0.19 |
| 47 | NHCH$_3$ | CH$_2$ | S | H | 2 | 1.9 |
| 48 | NHCH$_2$CH$_3$ | CH$_2$ | S | H | 2 | 1.0 |
| 49 | NH$_2$ | CH(CH$_2$CH(CH$_3$)$_2$) | S | H | 2 | 0.2 |
| 50 | NH$_2$ | CH$_2$ | O | H | 2 | 8.2 |
| 51 | NHCH$_3$ | CH$_2$ | O | H | 2 | 2.3 |
| 52 | NH$_2$ | CHCH$_3$ | O | 5-C$_6$H$_5$CH$_2$O | 2 | 0.25 |
| 53 | NHCH$_3$ | CHCH$_3$ | O | 5-C$_6$H$_5$CH$_2$O | 2 | 0.20 |
| 54 | NH$_2$ | CHCH$_3$ | NH | H | 2 | 2.9 |

*Position at which side chain is attached to the heterocyclic ring system.

EXAMPLE 75

Rat Peritoneal Anaphylaxis Model

Assays to determine the ability of compounds to prevent the synthesis of 5-lipoxygenase products in vivo after oral administration were performed as follows: Fasted male Sprague-Dawley derived rats (SASCO Inc., Oregon WI) were passively sensitized by i.p. injection of rabbit anti-bovine serum albumin (anti-BSA) in phosphate buffered saline (PBS), pH 7.1. Three hours after sensitization, the rats were injected i.p. with BSA (4 mg) in PBS (5 mL) containing 30 mM 1-cysteine. This initiates the synthesis of leukotrienes in the peritoneal cavity. Test compounds suspended in 0.2% methylcellulose or vehicle controls were administered by gavage 1 hour prior to the antigen challenge. Typically 6-8 rats were included in both the control and treatment groups.

The rats were sacrificed 15 minutes after challenge, the peritoneal cavity opened and the fluid contents collected with a plastic trocar. The cavities were rinsed with cold PBS, pH 7.4 , (5 mL) containing gelatin (5 mg), sodium azide (5 mg), EDTA (18.8 mg) and 1-cysteine (30 mM). These fluids were transferred to ice-cold methanol, incubated for about 20 minutes, vortexed and then centrifuged at 1000xg for 15 minutes. Fluid volumes were recorded and the samples stored frozen until radioimmunoassay (New England Nuclear, Boston, MA) for $LTC_4$ equivalents was conducted.

Analysis of variance followed by Duncan's multiple range test was used to determine the statistical significance of treatment effects. Percent inhibition values were determined by comparing the treatment values to the mean of the control group. Inhibitory potencies for representative examples of compounds of this invention are listed in Table 2. The results of this assay demonstrate that compounds of this invention prevent the in vivo biosynthesis of the products of 5-lipoxygenase action on arachidonic acid.

TABLE 2

| | In vivo 5-lipoxygenase inhibitory potency of compounds of this invention in the rat peritoneal anaphylaxis model after oral administration. | | |
|---|---|---|---|
| Example | % Inhibition at 200 μmole/kg PO | Example | % Inhibition at 200 μmole/kg PO |
| 1 | 67 | 28 | 67 |
| 2 | 98 | 29 | 89 |
| 3 | 79 | 30 | 79 |
| 4 | 78 | 31 | 30 |
| 5 | 79 | 32 | 35 |
| 9 | 26 | 34 | 84 |
| 10 | 69 | 35 | 69 |
| 13 | 53 | 36 | 85 |
| 14 | 76 | 46 | 33 |
| 15 | 75% at 100 μmole/kg | 47 | 77 |
| 16 | 81 | 48 | 73 |
| 17 | 59 | 49 | 66 |
| 18 | 47 | 51 | 81 |
| 19 | 61% at 150 μmole/kg | 52 | 46 |
| 20 | <40% | 53 | <40% |
| 22 | 91 | 54 | 76 |
| 23 | 60% at 100 μmole/kg | | |
| 25 | 72 | | |
| 26 | 56 | | |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

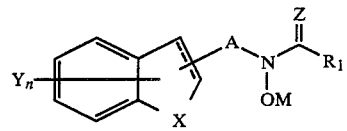

wherein $R_1$ is (1) hydrogen, (2) $C_1$ to $C_4$ alkyl, (3) $C_2$ to $C_4$ alkenyl, or (4) $NR_2R_3$, wherein $R_2$ and $R_3$ are independently selected from (1) hydrogen, (2) $C_1$ to $C_4$ alkyl and (3) hydroxyl, but $R_2$ and $R_3$ are not simultaneously hydroxyl;

wherein X is oxygen, sulfur, $SO_2$, or $NR_4$, wherein $R_4$ is (1) hydrogen, (2) $C_1$ to $C_6$ alkyl, (3) $C_1$ to $C_6$ alkoyl, (4) aroyl, or (5) alkylsulfonyl;

A is selected from $C_1$ to $C_6$ alkylene and $C_2$ to $C_6$ alkenylene;

n is 1-5;

Y is selected independently at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) $C_1$-$C_8$ thioalkyl, (11) aryl, (12) aryloxy, (13) aroyl, (14) $C_1$ to $C_{12}$ arylalkyl, (15) $C_2$ to $C_{12}$ arylalkenyl, (16) $C_1$ to $C_{12}$ arylalkoxy, (17) $C_1$ to $C_{12}$ arylthioalkoxy, and substituted derivatives of (18) aryl, (19) aryloxy, (20) aroyl, (21) $C_1$ to $C_{12}$ arylalkyl, (22) $C_2$ to $C_{12}$ arylalkenyl, (23) $C_1$ to $C_{12}$ arylalkoxy, or (24) $C_1$ to $C_{12}$ arylthioalkoxy, wherein substituents are selected from halo, nitro, cyano, $C_1$ to $C_{12}$ alkyl, alkoxy, and halosubstituted alkyl;

Z is oxygen or sulfur;

and M is hydrogen, a pharmaceutically acceptable cation, aroyl, or $C_1$ to $C_{12}$ alkoyl.

2. A compound of claim 1 having the formula:

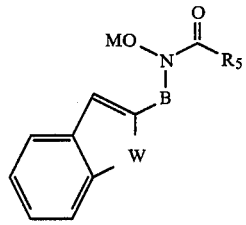

wherein $R_5$ is $C_1$ or $C_2$ alkyl, or $NR_6R_7$ where $R_6$ and $R_7$ are independently selected from hydrogen and $C_1$ or $C_2$ alkyl; B is $CH_2$ or $CHCH_3$; W is oxygen or sulfur; and M is hydrogen, a pharmaceutically acceptable cation, aroyl, or $C_1$ to $C_{12}$ alkoyl.

3. A compound according to claim 1 wherein $R_1$ is $CH_3$.

4. A compound according to claim 1 wherein $R_1$ is $NH_2$.

5. A compound according to claim 1 wherein $R_1$ is $NHCH_3$.

6. A compound according to claim 1 wherein A is —$CHCH_3$—.

7. A compound according to claim 1 wherein A is —$CH_2$—.

8. A compound according to claim 1 wherein X is sulfur.

9. A compound according to claim 1 wherein X is oxygen.

10. The compound of claim 1 having the formula:

11. The compound of claim 1 having the formula:

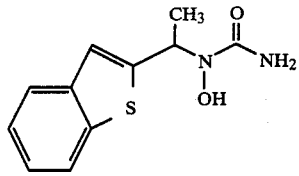

12. The compound of claim 1 having the formula:

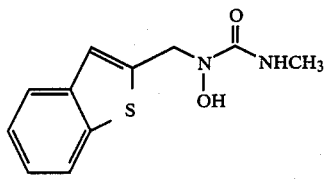

13. A method for inhibiting 5- and/or 12-lipoxygenase activity in a mammal in need of such treatment, comprising administering to the mammal a therapeutically effective amount of a compound of claim 1.

14. The method of claim 13 wherein the compound has the formula:

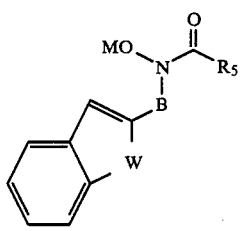

wherein $R_5$ is $C_1$ or $C_2$ alkyl, or $NR_6R_7$ are independently selected from hydrogen and $C_1$ or $C_2$ alkyl; B is $CH_2$ or $CHCH_3$; W is oxygen or sulfur; and M is hydrogen, a pharmaceutically acceptable cation, aroyl, or $C_1$ to $C_{12}$ alkoyl.

15. The method of claim 13 wherein $R_1$ is $CH_3$.
16. The method of claim 13 wherein $R_1$ is $NH_2$.
17. The method of claim 13 wherein $R_1$ is $NHCH_3$.
18. The method of claim 13 wherein A is —CHCH$_3$—.
19. The method of claim 13 wherein A is —CH$_2$—.
20. The method of claim 13 wherein X is sulfur.
21. The method of claim 13 wherein X is oxygen.
22. The method of claim 13 wherein the compound has the formula:

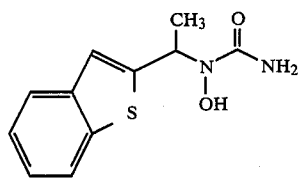

23. The method of claim 13 wherein the compound has the formula:

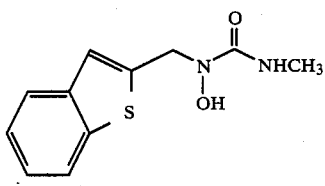

24. The method of claim 13 wherein the compound has the formula:

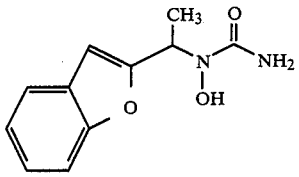

25. A pharmaceutical composition for inhibiting 5- and/or 12-lipoxygenase, comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 4,873,259

DATED : Oct. 10, 1989

INVENTOR(S) : James B. Summers, Jr., Bruce P. Gunn, Dee W. Brooks

It is certified that error appears in the above-identified patent and that said Letters Patent is hereby corrected as shown below:

Column 14, line 47; Replace "459" with --4.59--

Column 17, line 32: Replace "N-hydroxy-N-(1(1-methylindol-3-yl)ethyl)" with --"N-hydroxy-N-(1-(1-methylindol-3-yl)ethyl)--

Column 30, line 8: Replace "analysis" with --Analysis--

Column 30, line 24: Replace "(d,1,J=2.22);" with --(d,1,J=2.2);--

Column 37, line 47: After "$NR_6R_7$" and before "are" insert --where $R_6$ and $R_7$--

Signed and Sealed this

Fifteenth Day of May, 1990

Attest:

HARRY F. MANBECK, JR.

*Attesting Officer*    *Commissioner of Patents and Trademarks*

UNITED STATES PATENT AND TRADEMARK OFFICE

CERTIFICATE EXTENDING PATENT TERM
UNDER 35 U.S.C. § 156

PATENT NO.    :   4,873,259

ISSUED        :   October 10, 1989

INVENTOR(S)   :   James B. Summers, Jr. et al.

PATENT OWNER  :   Abbott Laboratories

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,398 days from February 10, 2007, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 2nd day of September 1998.

Bruce A. Lehman
Assistant Secretary of Commerce and
Commissioner of Patents and Trademarks